United States Patent [19]
Baum et al.

[11] Patent Number: 5,783,665
[45] Date of Patent: Jul. 21, 1998

[54] CYTOKINE WHICH IS A LIGAND FOR OX40

[75] Inventors: Peter R. Baum, Seattle; William C. Fanslow, III, Federal Way; Richard B. Gayle, Woodinville; Raymond G. Goodwin, Seattle, all of Wash.

[73] Assignee: Immunex Corporation, Seattle, Wash.

[21] Appl. No.: 494,574

[22] Filed: Jun. 22, 1995

Related U.S. Application Data

[62] Division of Ser. No. 97,827, Jul. 23, 1993, Pat. No. 5,457,035.

[51] Int. Cl.$^6$ .................................................. C07K 14/705
[52] U.S. Cl. .......................... 530/350; 530/351; 530/395; 514/12
[58] Field of Search ..................... 530/350, 351, 530/395, 403, 412; 536/23.5; 435/69.1, 69.7; 514/12

[56] References Cited

PUBLICATIONS

Paterson et al., *Mol. Immunol.* 24:1281; 1987.
Mallett et al., *EMBO J.* 9:1063, 1990.
Mallett and Barclay, *Immunlogy Today* 12:220; 1991.
Smith et al., *Biochem. Biophys. Res. Commun.* 176:335; 1991.
Miura et al., *Mol. Cell. Biol.* 11:1313; 1991.
Calderhead et al., J. Immunol 151:5261–5271; 1993 (Nov.).

*Primary Examiner*—Lorraine M. Spector
*Attorney, Agent, or Firm*—Patricia Anne Perkins

[57] ABSTRACT

There is disclosed a polypeptide (OX40-L) and DNA sequences, vectors and transformed host cells useful in providing OX40-L polypeptides. More particularly, this invention provides isolated murine OX40-L polypeptides that bind to the extracellular binding region of OX40.

3 Claims, 4 Drawing Sheets

CYTOKINE WHICH IS A LIGAND FOR OX40

CROSS-REFERENCE TO RELATED APPLICATIONS

This application is a divisional of U.S. Ser. No. 08/097,827, filed Jul. 23, 1993, issued as U.S. Pat. No. 5,457,035 on Oct. 10, 1995.

TECHNICAL FIELD OF THE INVENTION

The present invention relates to a novel cytokine. More specifically, the present invention relates to the cloning of a cytokine that binds to OX40.

BACKGROUND OF THE INVENTION

Cytokines are hormone-like factors that are active in regulating the survival, growth, differentiation and activity of various types of cells. Numerous cytokines have been described, and some of their functions elucidated. Several cytokines appear to be important in hematopoiesis, the process whereby pluripotent hematopoietic stem cells give rise to highly differentiated, mature blood cells that perform very specific functions (reviewed in Metcalf, D. 1984. *The Hemopoietic Colony Stimulating Factors*. Elsevier, Amsterdam, 486 pp). Cytokines designated "Interleukins" influence immune effector cells.

OX40 is a membrane glycoprotein with an approximate $M_r$ of 47–51 Kd that is present on the CD4+ subset of activated rat T cells (Paterson et al., *Mol. Immunol.* 24:1281; 1987). Mallett et al. (*EMBO J.* 9:1063, 1990) report the cloning and characterization of OX40, and the similarity of this membrane glycoprotein to the low affinity nerve growth factor receptor (NGFR). NGFR and OX40 are members of a superfamily of cell surface proteins defined by the presence of cysteine-rich motifs in the extracellular region (Mallett and Barclay, *Immunlogy Today* 12:220; 1991). This superfamily includes the B cell antigen CD40, the lymphocyte antigen CD27, CD30 (an antigen found on Hodgkin's lymphoma and Reed-Sternberg cells), two receptors for Tumor Necrosis Factor (TNF), a murine protein referred to as 4-1BB, and proteins encoded by the T2 open reading frame (ORF) of Shope fibroma virus (along with the equivalent proteins from other pox viruses) (Smith et al., *Biochem. Biophys. Res. Commun.* 176:335; 1991).

Prior to the present invention, a ligand for OX40 was unknown. Accordingly, there is a need in the art to identify and characterize an OX40 ligand (OX40-L).

SUMMARY OF THE INVENTION

The present invention comprises an isolated DNA molecule having a nucleotide sequence represented by nucleotides 148 through 741 of SEQ ID NO:1, and their complements, which encodes a novel cytokine, OX40-L, that binds to a cell surface molecule referred to as OX40. The deduced amino acid sequence encoded by the novel DNA molecule is disclosed in SEQ ID NO:1 and SEQ ID NO:2. The present invention further comprises other DNA molecules that hybridize, under moderate or severe stringency conditions, to the DNA molecule defined by nucleotides 148 through 741 of SEQ ID NO:1 and their complements. The invention further comprises DNA molecules which, due to the degeneracy of the genetic code, differ from the aforementioned DNA molecules but which encode polypeptides that bind OX40, and sequences complementary to them.

In addition, the present invention provides recombinant expression vectors comprising the inventive DNA molecules, and host cells transfected or transformed with the expression vectors. Methods of using the transformed or transfected host cells to produce recombinant proteins having OX40 binding activity are also provided.

The present invention further comprises OX40-L polypeptides, encoded by the inventive DNA molecules, which are capable of binding OX40. OX40-L is a type II membrane polypeptide having an extracellular region at its C-terminus, a transmembrane region and an intracellular region at its N-terminus. Soluble OX40-L comprises an extracellular region of OX40-L or a fragment thereof. The amino acid sequence of murine OX40-L is described in SEQ ID NO:2. The extracellular region of murine OX40-L extends from amino acid 49 to amino acid 198 of SEQ ID NO:2. OX40-L biological activity is mediated by binding of this cytokine with OX40 and includes co-stimulation of murine T cells (stimulation in the presence of suboptimal levels of a mitogen), and induction of Interleukin-2 (IL-2) and Interleukin-4 secretion (IL-4).

The present invention further provides antisense or sense oligonucleotides (deoxyribonucleotides or ribonucleotides) that correspond to a sequence of at least about 12 nucleotides selected from the nucleotide sequence of OX40-L, or DNA or RNA sequences complementary to the nucleotide sequence of OX40-L as described in SEQ ID NO:1. Such antisense or sense oligonucleotides prevent transcription or translation of OX40-L mRNA or polypeptides.

Further still, the present invention provides OX40-L peptide fragments that correspond to a protein sequence of at least 10 amino acids selected from the amino acid sequence encoded by SEQ ID NO:1 that can act as immunogens to generate antibodies specific to the OX40-L immunogens. Such OX40-L immunogen fragments can serve as antigenic determinants in providing monoclonal antibodies specific for OX40-L.

DETAILED DESCRIPTION OF THE INVENTION

Figure 1:
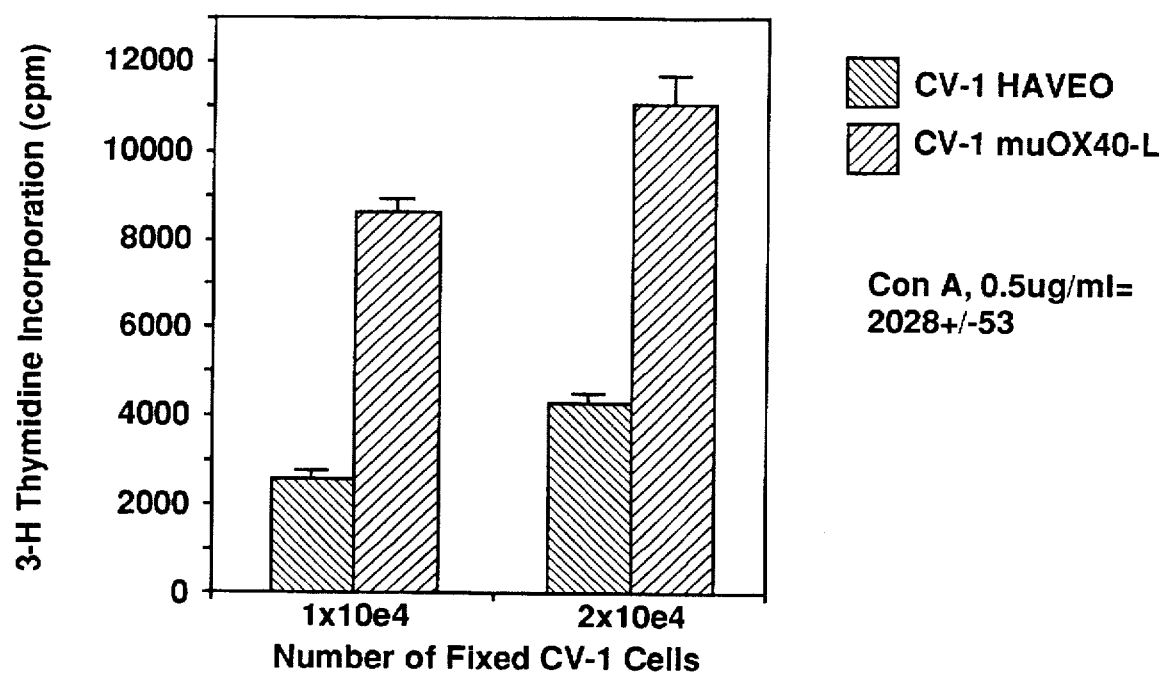
FIG. 1 illustrates the effect of fixed CV-1/EBNA cells transfected with an expression vector encoding mouse OX40-L versus fixed CV-1/EBNA cells transfected with vector alone on the proliferation of mouse T cells in the presence of a suboptimal level of mitogen (0.5 µg/l Concanavalin A).

A DNA molecule encoding a novel polypeptide that can act as a ligand for murine T cell antigen OX40 has been isolated and sequenced. More particularly, the present invention comprises isolated DNA molecules encoding OX40-L selected from the group consisting of (a) nucleotides 148 through 741 of the nucleotide sequence set forth in SEQ ID NO:1, and their complements, (b) DNA sequences which hybridize to the DNA sequences of (a) under conditions of moderate stringency and which encode an OX40-L polypeptide capable of binding OX40, and (c) DNA sequences which, due to the degeneracy of the genetic code, encode OX40-L polypeptides encoded by any of the foregoing DNA sequences, and their complements. In addition, the present invention includes expression vectors comprising DNA sequences encoding OX40-L polypeptides, and host cells transfected or transformed with such vectors. Further provided are methods of using the transfected or transformed host cells to express recombinant OX40-L polypeptides.

OX40-L polypeptides include other forms of mammalian OX40-L, such as derivatives or analogs of murine OX40-L, and mammalian homologs of murine OX40-L. Murine OX40-L comprises a 150 amino acid extracellular region at the C-terminus of full length, membrane-bound polypeptide. The extracellular region contains the domain that binds to OX40. Murine OX40-L further comprises a putative hydrophobic 20 amino acid transmembrane region delineated by charged amino acids on either side and a 28 amino acid intracellular region at the N-terminus. The present invention further comprises full length OX40-L polypeptides, or fragments thereof comprising all or part of the extracellular region.

Full-length OX40-L is a type II polypeptide having its N-terminus as its intracellular domain, followed by a transmembrane region, and an extracellular domain at the C-terminus of the polypeptide. The extracellular domain, which is longer than either the intracellular domain or the transmembrane region, contains one potential N-linked glycosylation site and two potential disulfide bonds in view of four cysteine (Cys) residues in the extracellular region. A soluble version of OX40-L can be made from the extracellular region or a fragment thereof. The extracellular region of murine OX40-L extends from amino acid 49 to amino acid 198 of SEQ ID NOs:1 and 2.

The novel cytokine disclosed herein is a ligand for OX40, a receptor that is a member of the TNF receptor super family. Therefore, OX40-L is likely to be responsible for transducing signal via OX40, which is known to be expressed, for example, by T lymphocytes. The biological activity of OX40-L is mediated by binding to OX40 or a species-specific homolog thereof and comprises stimulation of T cells in the presence of sub-optimal levels of a mitogen such as Concanvalin A (Con A) or phytohemagglutinin (PHA). OX40-L also acts as a potent co-stimulus in the induction of IL-2 and IL-4 secretion, and is useful in culturing primary T cells for development of clonal T cell lines.

The nucleotide sequence of the coding region of the DNA encoding OX40-L exhibits 73% similarity to a nucleotide sequence from a coding region of a DNA encoding a protein designated gp34 (Miura et al., *Mol. Cell. Biol.* 11:1,313; 1991), using the BESTFIT program (University of Wisconsin Genetics Computer Group, Madison, Wis., USA). gp34 is a glycoprotein expressed in cells infected with human T-cell leukemia virus type I (HTLV-I); according to BEST-FIT analysis, OX40-L and gp34 are 62% similar on the amino acid level.

Nucleic acid molecules within the scope of the present invention include DNA and/or RNA molecules that hybridize to the DNA molecule represented by SEQ ID NO:1 and its complementary strand, under conditions of moderate or severe stringency, and which encode OX40-L polypeptides that are capable of binding OX40. Moderate stringency hybridization conditions refer to conditions described in, for example, Sambrook et al. *Molecular Cloning: A Laboratory Manual*, 2 ed. Vol. 1, pp. 1.101–104, Cold Spring Harbor Laboratory Press, (1989). Conditions of moderate stringency, as defined by Sambrook et al., include use of a prewashing solution of 5×SSC, 0.5% SDS, 1.0 mM EDTA (pH 8.0) and hybridization conditions of 50° C., 5×SSC, overnight. Conditions of severe stringency include higher temperatures of hybridization and washing. Such hybridizing DNA molecules differ from the DNA molecule represented by SEQ ID NO:1 because of one or a plurality of deletions, insertions or substitutions of nucleotides, and can be prepared by oligonucleotide synthesis and ligation or by site-specific mutagenesis techniques.

OX40-L refers to a genus of polypeptides which are capable of binding OX40, or mammalian homologs of OX40. As used herein, the term "OX40-L" includes soluble OX40-L polypeptides lacking transmembrane and intracellular regions, mammalian homologs of OX40-L, analogs of OX40-L or derivatives of OX40-L. OX40-L may also be obtained by mutations of nucleotide sequences coding for an OX40-L polypeptide. An OX40-L analog, as referred to herein, is a polypeptide encoded by a DNA molecule capable of hybridizing to the DNA molecule represented by SEQ ID NO:1 under conditions of moderate stringency.

The primary amino acid structure of human or murine OX40-L may be modified to create OX40-L derivatives by forming covalent or aggregative conjugates with other chemical moieties, such as glycosyl groups, lipids, phosphate, acetyl groups and the like, or by creating amino acid sequence mutants. Covalent derivatives of OX40-L are prepared by linking particular functional groups to OX40-L amino acid side chains or at the N-terminus or C-terminus of a OX40-L polypeptide or the extracellular domain thereof, or to carbohydrate moieties present on OX40-L polypeptides.

Other OX40-L polypeptides within the scope of this invention include covalent or aggregative conjugates of OX40-L or its fragments with other proteins or polypeptides, such as by synthesis in recombinant culture as N-terminal or C-terminal fusions. For example, the conjugate may comprise a signal or leader polypeptide sequence at the N-terminal region or C-terminal region of a OX40-L polypeptide which co-translationally or post-translationally directs transfer of the conjugate from its site of synthesis to a site inside or outside of the cell membrane or cell wall (e.g., a human or murine Interleukin-7 leader sequence, or an α-factor leader of Saccharomyces). OX40-L polypeptide fusions can comprise polypeptides added to facilitate purification and identification of OX40-L (e.g. poly-His), or fusions with other cytokines to provide novel polyfunctional entities. Other cytokines include, for example, any of the interleukins, TNF (tumor necrosis factor), GM-CSF (granulocyte macrophage-colony stimulating factor), G-CSF (granulocyte-colony stimulating factor), MGF (mast cell growth factor), EGF (epidermal growth factor), PDGF (platelet-derived growth factor), NGF (nerve growth factor), EPO (erythropoietin), γ-IFN (gamma interferon), 4-1BB-L (4-1BB ligand) and other cytokines that affect immune cell growth, differentiation or function.

Biological activity of OX40-L may be determined, for example, by competition for binding to the ligand binding domain of OX40 (i.e. competitive binding assays). One configuration of a competitive binding assay for OX40-L polypeptide uses a radiolabeled, soluble murine OX40-L according to SEQ ID NO:1, and intact cells expressing OX40 (e.g., activated murine CD4$^+$ T cells). Instead of intact cells, one could substitute soluble OX40 (such as a OX40/Fc fusion protein) bound to a solid phase through a Protein A or Protein G interaction with the Fc region of the fusion protein. A second configuration of a competitive binding assay utilizes radiolabeled soluble OX40 such as an OX40/Fc fusion protein, and intact cells expressing OX40-L. Alternatively, soluble OX40-L could be bound to a solid phase.

Competitive binding assays can be performed using standard methodology. For example, radiolabeled murine OX40-L can be used to compete with a putative OX40-L homolog to assay for binding activity against surface-bound OX40. Qualitative results can be obtained by competitive autoradiographic plate binding assays, or fluorescence activated cell sorting, or Scatchard plots may be utilized to generate quantitative results.

Competitive binding assays with intact cells expressing OX40 can be performed by two methods. In a first method, CD4+ T cells are grown are cultured and activated according to standard methodology (for example, as described in Grabstein et al., *J. Immunol.* 150:3141, 1993). In a second method, transfected cells expressing full length, membrane-bound OX40 with an extracellular region exterior to the cell can be used.

Alternatively, soluble OX40 can be bound to a solid phase such as a column chromatography matrix, or a tube or similar substrate suitable for analysis for the presence of a detectable moiety such as $^{125}$I. Binding to a solid phase can be accomplished, for example, by obtaining a OX40/Fc fusion protein and binding it to a protein A or protein G surface.

Another means to measure the biological activity of OX40-L and homologs thereof is to utilize conjugated, soluble OX40 (for example, $^{125}$I-OX40/Fc) in competition assays similar to those described above. In this case, however, intact cells expressing OX40-L, or soluble OX40-L bound to a solid substrate, are used to measure competition for binding of conjugated, soluble OX40 to OX40-L by a sample containing a putative OX40 homolog.

OX40-L may also be assayed by measuring biological activity in a T cell proliferation assay. Briefly, purified T cells are obtained by methods that are known in the art. The purified T cells are incubated in the presence of membrane-bound OX40-L and a suboptimal level of a mitogen such as Con A or PHA. Proliferation is determined by measuring the incorporation of a radiolabeled substance such as $^3$H thymidine according to standard methods.

Yet another assay for determining OX40-L biological activity is induction of the secretion of IL-2 and IL-4 by T cells. T cells are purified and stimulated with OX40-L in the presence of a suboptimal level of a mitogen as described previously. Induction of IL-2 secretion is determined by bioassay, measuring the proliferation of an IL-2 dependent cell line. Similarly, induction of IL-4 secretion is determined by measuring the proliferation of an IL-4 dependent cell line.

OX40-L can be used in a binding assay to detect cells expressing OX40 or homologs thereof. For example, murine OX40-L according to SEQ ID NO:1, or an extracellular domain or a fragment thereof, can be conjugated to a detectable moiety such as $^{125}$I. Radiolabeling with $^{125}$I can be performed by any of several standard methodologies that yield a functional $^{125}$I-OX40-L molecule labeled to high specific activity. Alternatively, another detectable moiety such as an enzyme that can catalyze a colorimetric or fluorometric reaction, biotin or avidin may be used. The conjugated OX40-L is diluted into a suitable medium. Cells expressing OX40 or an OX40 homolog are incubated with the medium containing the conjugated OX40-L. After incubation, unbound conjugated OX40-L is removed and binding is measured using the detectable moiety.

OX40-L polypeptides may exist as oligomers, such as dimers or trimers. Oligomers may be linked by disulfide bonds formed between cysteine residues on different OX40-L polypeptides. Alternatively, one can link two soluble OX40-L domains with a linker sequence, such as those described in U.S. Pat. No. 5,073,627, which is incorporated by reference herein. OX40-L polypeptides may also be created by fusion of the C terminal of soluble OX40-L (extracellular domain) to the Fc region of IgG1 (for example, as described in Fanslow et al., *J. Immunol.* 149:655; 1992). OX40-L/Fc fusion proteins are allowed to assemble much like heavy chains of an antibody molecule to form divalent OX40-L. If fusion proteins are made with both heavy and light chains of an antibody, it is possible to form an OX40-L oligomer with as many as four OX40-L extracellular regions. Alternatively, oligomeric OX40-L proteins may be created by fusion of the C terminal domain of OX40Lwith a leucine zipper peptide that spontaneously oligomerizes.in solution, as described in U.S. Ser. No. 07/969, 703, filed Oct. 23, 1992, the disclosure of which is hereby incorporated by reference.

Fusion proteins can be prepared using conventional techniques of enzyme cutting and ligation of fragments from desired sequences. PCR techniques employing synthetic oligonucleotides may be used to prepare and/or amplify the desired fragments. Overlapping synthetic oligonucleotides representing the desired sequences can also be used to prepare DNA constructs encoding fusion proteins. Fusion proteins can also comprise OX40-L and two or more additional sequences, including a leader (or signal peptide) sequence, Fc region, linker sequence, a leucine zipper sequence, and sequences encoding highly antigenic moieties that provide a means for facile purification or rapid detection of a fusion protein.

Signal peptides facilitate secretion of proteins from cells. An exemplary signal peptide is the amino terminal 25 amino acids of the leader sequence of murine interleukin-7 (IL-7; Namen et al., *Nature* 333:571; 1988). Other signal peptides may also be employed furthermore, certain nucleotides in the IL-7 leader sequence can be altered without altering the amino acid sequence. Additionally, amnino acid changes that do not affect the ability of the IL-7 sequence to act as a leader sequence can be made.

The Flag® octapeptide (Asp-Tyr-Lys-Asp-Asp-Asp-Asp-Lys) does not alter the biological activity of fusion proteins, is highly antigenic and provides an epitope reversibly bound by a specific monoclonal antibody, enabling rapid detection and facile purification of the expressed fusion protein. The Flag® sequence is also specifically cleaved by bovine mucosal enterokinase at the residue immediately following the Asp-Lys pairing. Fusion proteins capped with this peptide may also be resistant to intracellular degradation in *E. coli*. A murine monoclonal antibody that binds the Flag® sequence has been deposited with the ATCC under accession number HB 9259; methods of using the antibody in purification of fusion proteins comprising the Flag® sequence are described in U.S. Pat. No. 5,011,912, which is incorporated by reference herein.

Suitable Fc regions are defined as Fc regions that can bind to protein A or protein G, or alternatively, are recognized by an antibody that can be used in purification or detection of a fusion protein comprising the Fc region. Preferable Fc regions include the Fc region of human IgG$_1$ or murine IgG$_1$. One example is the human IgG$_1$ Fc mutein shown in SEQ ID NOs:10 and 11; another example is an Fc region encoded by cDNA obtained by PCR as described by Fanslow et al., *J. Immunol.* 149:65 (1992). Portions of a suitable Fc region may also be used, for example, an Fc region of human IgG$_1$ from which has been deleted a sequence of amino acids responsible for binding to protein A, such that the resultant Fc region binds to protein G but not protein A.

OX40-L may be linked directly to another protein to form a fusion protein; alternatively, the OX40-L and the other protein may be separated by a distance sufficient to ensure that the OX40-L properly folds into its secondary and tertiary structures. Suitable linker sequences (1) will adopt a flexible extended conformation, (2) will not exhibit a propensity for developing an ordered secondary structure which could interact with the functional domains of fusion proteins, and (3) will have minimal hydrophobic or charged character which could promote interaction with the functional protein domains. Typical surface amino acids in flexible protein regions include Gly, Asn and Ser. Virtually any permutation of amino acid sequences containing Gly, Asn and Ser would be expected to satisfy the above criteria for a linker sequence. Other near neutral amino acids, such as Thr and Ala, may also be used in the linker sequence. The length of the linker sequence may vary without significantly affecting the biological activity of the fusion protein. Linker sequences are unnecessary where the proteins being fused have non-essential N- or C-terminal amino acid regions which can be used to separate the functional domains and prevent steric interference. Exemplary linker sequences are described in U.S. Pat. Nos. 5,073,627 and 5,108,910, the disclosures of which are hereby incorporated by reference.

OX40-L polypeptides may exist as soluble polypeptides comprising the extracellular domain of OX40-L as shown in SEQ ID NOs:1 and 2, amino acids 49 through 198, or as membrane-bound polypeptides comprising the extracellular domain, a transmembrane region and a short intracellular domain, as shown in SEQ ID NOs: 1 and 2, amino acids 1 through 198. Moreover, the present invention comprises oligomers of OX40-L extracellular domains or fragments thereof, linked by disulfide interactions, or expressed as fusion polymers with or without spacer amino acid linking groups. For example, a dimer OX40-L molecule can be linked by an IgG Fc region linking group.

The ability of OX40-L to co-stimulate T cell proliferation and cytokine secretion suggests a role for OX40-L as an autocrine growth ligand in T cell activation. Furthermore, native OX40-L is a plasma membrane protein, and may be involved in direct cell-dependent interactions between T cells. Thus, the OX40/OX40-L interaction may comprise a component of the adhesion of T cells to one another that is seen following activation with antigen or mitogen. Moreover, the stimulation of IL-2 and IL-4 secretion suggests that OX40-L has its effect upon the TH0 and/or TH2 subpopulations of T cells (Mosmann and Coffman, *Immunol. Today* 8:223, 1987; Mosmann and Coffman, *Adv. Immunol.* 46:111, 1988). It is known in the art that generation of TH2 versus TH1 populations of T cells will have an effect upon the type and effectiveness of the ensuing immune response (Coffman et al., *Immuno. Rev.* 123:189; 1991). The ability of OX40-L to induce both IL-2 and IL-4 indicates that OX40-L has the potential to modify a number of immune responses, including the nature of the immunoglobulin isotype generated and the development of cytolytic T cells. Therefore, OX40-L is likely to be useful in inducing a TH2 immune response, for example as a vaccine adjuvant, or in ex vivo techniques to stimulate selected populations of TH2 cells. An OX40-L antagonist may similarly be useful in directing an immune response toward a TH1 response or in inhibiting TH2 responses. OX40-L will also be useful as an in vitro reagent for the culture of primary T cells and the development of clonal T cell lines, or for the detection of cells expressing OX40 or an OX40 homolog.

The present invention further includes OX40-L polypeptides with or without associated native-pattern glycosylation. OX40-L expressed in yeast or mammalian expression systems (e.g., COS-7 cells) may be similar to or significantly different from a native OX40-L polypeptide in molecular weight and glycosylation pattern, depending upon the choice of expression system. Expression of OX40-L polypeptides in bacterial expression systems, such as *E. coli*, provides non-glycosylated molecules.

DNA constructs that encode various additions or substitutions of amino acid residues or sequences, or deletions of terminal or internal residues or sequences not needed for biological activity or binding can be prepared. For example, the extracellular OX40-L N-glycosylation site at amino acid residues 91–93 can be modified to preclude glycosylation while allowing expression of a homogeneous, reduced carbohydrate analog using yeast expression systems. N-glycosylation sites in eukaryotic polypeptides are characterized by an amino acid triplet Asn-X-Y, wherein X is any amino acid except Pro and Y is Ser or Thr. Appropriate modifications to the nucleotide sequence encoding this triplet will result in substitutions, additions or deletions that prevent attachment of carbohydrate residues at the Asn side chain.

In another example, sequences encoding Cys residues can be altered to cause the Cys residues to be deleted or replaced with other amino acids, preventing formation of incorrect intramolecular disulfide bridges upon renaturation. Human OX40-L comprises four Cys residues in its extracellular domain, and two Cys residues within the putative transmembrane region. One or more of the Cys residues in the transmembrane region can be replaced with another amino acid or deleted without affecting protein tertiary structure or disulfide bond formation.

Furthermore, nucleotides encoding the intracellular region and transmembrane region of OX40-L may be deleted, resulting in a soluble OX40-L. Nucleotides encoding additional amino acids may be deleted from the ends of a DNA encoding the extracellular region of OX40-L, resulting in truncated forms of soluble OX40-L. For example, a DNA encoding a polypeptide defined by a sequence beginning with an amino acid in the sequence between amino acid 49 and amino acid 69, inclusive, through and including an amino acid in the sequence between amino acid 164 and amino acid 198, inclusive, of the sequence set forth in SEQ ID NO:2 can be prepared. Such a DNA will still encode an OX40-L polypeptide having the four Cys residues present in the extracellular region of native OX40-L. DNAs encoding soluble OX40-L may further comprise nucleotides encoding signal peptides, linker sequences, peptides that facilitate purification or peptides that allow oligomerization, as described herein.

Other approaches to mutagenesis involve modification of sequences encoding dibasic amino acid residues to enhance expression in yeast systems in which KEX2 protease activity is present. Sub-units of a OX40-L polypeptide may be constructed by deleting sequences encoding terminal or internal residues or sequences.

OX40-L polypeptides are encoded by multi-exon genes. The present invention further includes alternative mRNA constructs which can be attributed to different mRNA splicing events following transcription and which share regions of identity or similarity with the cDNAs disclosed herein.

Antisense or sense oligonucleotides comprise a single-stranded nucleic acid sequence (either RNA or DNA) capable of binding to target OX40-L sequences. Antisense or sense oligonucleotides, according to the present invention, comprise a fragment of SEQ ID NO:1, or a DNA or RNA complement of SEQ ID NO:1 which comprises at least about 14 nucleotides. Preferably, such a fragment comprises from about 14 to about 30 nucleotides. The ability to create an antisense or a sense oligonucleotide, based upon a cDNA sequence for OX40-L is described in, for example, Stein and Cohen, Cancer Res. 48:2659, 1988 and van der Krol et al., BioTechniques 6:958, 1988. Binding of antisense or sense oligonucleotides to target nucleic acid sequences results in the formation of complexes that block translation (RNA) or transcription (DNA) by one of several means, including enhanced degradation of the complexes, premature termination of transcription or translation, or by other means.

Antisense or sense oligonucleotides further comprise oligonucleotides having modified sugar-phosphodiester backbones that are resistant to endogenous nucleases (described in WO91/06629), or which are covalently linked to organic moieties, such as those described in WO 90/10448, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, CaPO$_4$-mediated DNA transfection, electroporation, or gene transfer vectors such as Epstein-Barr virus or suitable retroviral vectors such as those described in PCT application U.S. Ser. No. 90/02656. Sense or antisense oligonucleotides may also be introduced into a cell containing the target nucleotide sequence by formation of a conjugate with a ligand binding molecule (for example, cell surface receptors, growth factors, cytokines, or other ligands that bind to cell surface receptors), as described in WO 91/04753. Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

The sequence of murine OX40-L cDNA was obtained by direct expression techniques by first obtaining a clone of the extracellular region of mouse OX40 (the receptor) by polymerase chain reaction (PCR) techniques using primers based upon a sequence for rat OX40 published in Mallett et al., EMBO J. 9:1063 (1990). The sequence of the extracellular domain of the mouse OX40 cloned by this method is shown in SEQ ID NOs:6 and 7. The upstream oligonucleotide (represented by SEQ ID NO:3) comprises a recognition site for the restriction endonuclease Spe I (nucleotides 3–8) upstream of a sequence encoding the first six (N-terminal) amino acids of OX40 (nucleotides 13–30). The downstream oligonucleotide (represented by SEQ ID NO:4) comprises a recognition site for the restriction endonuclease Spe I (nucleotides 3–8) upstream of a sequence encoding the last five (C-terminal) amino acids of OX40 (nucleotides 10–24).

The PCR product was digested with Spe I, and an approximately 800 bp fragment was isolated by gel filtration, and used in a second round of PCR reaction. The isolated fragment was ligated into Spe I cut plasmid, pBLUESCRIPT SK® (Stratagene Cloning Systems, La Jolla, Calif.), which was used to PCR an extracellular region of murine OX40 using the oligonucleotide primers represented in SEQ ID NO:3 and SEQ ID NO:5. The oligonucleotide defined by SEQ ID NO:5 deletes the C-terminal five amino acids of the region of murine OX40 that corresponds to the extracellular region of rat OX40 as described by Mallett et al., and includes a Bgl II site, and a sequence encoding two amino acids from the N-terminal of an Fc region of a human IgG$_1$.

The PCR product was used in a three-way ligation of the murine OX40 extracellular region and DNA encoding a human IgG Fc (as described in U.S. Ser. No. 07/969,703) into Sal I/Not I cut pBLUESCRIPT SK®. After amplification in E. coli, the insert encoding the OX40/Fc fusion protein was digested with Sal I/Not I, and cloned into plasmid pDC406 (McMahan et al., EMBO J. 10:2821, 1991). Site-directed mutagenesis, essentially as described by Deng and Nickoloff, Anal. Biochem. 200:81 (1992) was used to change three amino acid residues in the Fc region (Leu234 to Ala, Leu235 to Glu and Gly237 to Ala, using the amino acid numbering of Canfield and Morrison, J. Exp. Med. 173:1,483; 1991). The resulting OX40/Fc mutein exhibited reduced affinity for immunoglobulin receptors.

Other fusion proteins comprising ligand binding domains from other receptors can be made by obtaining a DNA sequence for the ligand binding domain of a receptor and fusing this sequence to a DNA sequence encoding an Fc region of an antibody molecule that binds to protein A or protein G, or another polypeptide that is capable of affinity purification, for example, avidin or streptavidin. The resultant gene construct can be introduced into mammalian cells to transiently express a fusion protein. Receptor/Fc fusion proteins can be purified by protein A or protein G affinity purification. Receptor/avidin fusion proteins can be purified by biotin affinity chromatography. The fusion protein can later be removed from the column by eluting with a high salt solution or another appropriate buffer.

Receptor/Fc fusion molecules preferably are synthesized in recombinant mammalian cell culture because they are generally too large and complex to be synthesized by prokaryotic expression methods. Examples of suitable mammalian cells for expressing a receptor/Fc fusion protein include CV-1 cells (ATCC CRL 70), COS-7 cells (ATCC CRL 1651), both derived from monkey kidney, and CV-1/EBNA cells (ATCC CRL 10478). The CV-1/EBNA cell line was derived by transfection of the CV-1 cell line with a gene encoding Epstein-Barr virus nuclear antigen-1 (EBNA-1) and constitutively express EBNA-1 driven from human CMV immediate-early enhancer/promoter. An EBNA-1 gene allows for episomal replication of expression vectors, such as pDC406, that contain the EBV origin of replication.

Large scale cultures of transfected cells were grown to accumulate supernatant from cells expressing OX40/Fc mutein. OX40/Fc mutein in supernatant fluid was purified by affinity purification using a protein A antibody affinity column (BioRad, Richmond, Calif., USA). The nucleotide and amino acid sequence of OX40/Fc mutein are shown in SEQ ID NOs:10 and 11. Several cell lines were screened using OX40/Fc muteini and FITC-labeled goat anti-human IgG antibody by flow cytometry. A clonal cell line, S49.1 (ATCC TIB 128), a murine T cell lymphoma line was found to express approximately 1,000 molecules of putative OX40-L per cell.

A cDNA expression library was made essentially as described in US Pat. No. 4,968,6507, from PMA-stimulated S49.1 cells. Briefly, cDNA was synthesized, inserted into empty pDC410 vector (a derivative of pDC406 (McMahan et al. *EMBO J.* 10:2821, 1991) with a unique Bgl II site and bearing the SV40 T antigen gene) and transformed into *E. coli*. Transformants were pooled, and the DNA from the pools was isolated and transfected into CV-1/EBNA cells to create an expression cloning library. Transfected CV-1/EBNA cells were cultured to permit transient expression of OX40-L. The transfected cells were then incubated with OX40/Fc mutein, followed by radio-iodinated murine anti-human IgG Fc (F(ab)$_2$, with wash steps to remove non-specifically bound material, and fixed with gluteraldehyde. The fixed slides were dipped in liquid photographic emulsion and exposed in the dark. After developing the slides, they were individually examined with a microscope and cells expressing OX40-L were identified by the presence of dark autoradiographic silver grains against a light background.

The expression cloning library was screened and four pools, containing approximately 2000 individual clones, were identified as positive for binding OX40/Fc mutein. One pool was broken down into smaller pools of approximately 250 colonies. The smaller pools were screened as described above. One of the smaller pools was positive for OX40-L.

A first clone was isolated and sequenced by standard techniques, to provide the cDNA sequence and deduced amino acid sequence of murine OX40-L. Sequencing results indicated an open reading fame upstream of the putative initiator methionine. A second, longer clone was isolated by screening colonies from the sub-pools by colony hybridization with a radioactive OX40-L probe, generated from the first clone. The cDNA insert in the longer clone was extended by 110 bp in the 5' region of the OX40-L cDNA. The nucleotide and deduced amino acid sequence of the second, longer clone are shown in SEQ ID NOs:1 and 2.

One can utilize the murine OX40-L cDNA sequences disclosed herein to obtain cDNAs encoding other mammalian homologs of murine OX40-L by cross-species hybridization techniques. Briefly, an oligonucleotide probe is created from the nucleotide sequence of the extracellular region of murine OX40-L as shown in SEQ ID NO:1. This probe can be made by standard techniques, such as those described in Maniatis et al., *Molecular Biology. A Laboratory Maiiual*, Cold Spring Harbor Laboratory, N.Y., 1982, pages 316-328. The murine probe is used to screen a mammalian cDNA library or genomic library under moderate stringency conditions. Examples of mammalian cDNA or genomic libraries include, for cDNA, a library made from the mammal's peripheral blood lymphocytes. Alternatively, various cDNA libraries or mRNAs isolated from various cell lines can be screened by Northern hybridization to determine a suitable source of mammalian OX40-L DNA or mRNA.

Recombinant expression vectors for expression of OX40-L by recombinant DNA techniques include a OX40-L DNA sequence comprising a synthetic or cDNA-derived DNA fragment encoding a OX40-L polypeptide, operably linked to a suitable transcriptional or translational regulatory nucleotide sequence, such as one derived from a mammalian, microbial, viral, or insect gene. Examples of regulatory sequences include sequences having a regulatory role in gene expression (e.g., a transcriptional promoter or enhancer), optionally an operator sequence to control transcription, a sequence encoding an mRNA ribosomal binding site, and appropriate sequences which control transcription and translation initiation and termination. Nucleotide sequences are operably linked when the regulatory sequence functionally relates to the OX40-L DNA sequence. Thus, a promoter nucleotide sequence is operably linked to a OX40-L DNA sequence if the promoter nucleotide sequence controls the transcription of the OX40-L DNA sequence. Still further, a ribosome binding site may be operably linked to a sequence for a OX40-L polypeptide if the ribosome binding site is positioned within the vector to encourage translation. In addition, sequences encoding signal peptides can be incorporated into expression vectors. For example, a DNA sequence for a signal peptide (secretory leader) may be operably linked to a OX40-L DNA sequence. The signal peptide is expressed as a precursor amino acid sequence which enables improved extracellular secretion of translated fusion polypeptide by a yeast host cell. An exemplary vector is pDC406, which includes regulatory sequences derived from SV40, human immunodeficiency virus (HIV), and Epstein-Barr virus (EBV).

Suitable host cells for expression of OX40-L polypeptides include prokaryotes, yeast or higher eukaryotic cells. Prokaryotes include gram negative or gram positive organisms, for example, *E. coli* or Bacilli. Suitable prokaryotic host cells for transformation include, for example, *E. coli, Bacillus subtilis, Salmonella typhimurium*, and various other species within the genera Pseudomonas, Streptomyces, and Staphylococcus. Higher eukaryotic cells include established cell lines of mammalian origin. Cell-free translation systems could also be employed to produce OX40-L polypeptides using RNAs derived from DNA constructs disclosed herein. Appropriate cloning and expression vectors for use with bacterial, fungal, yeast, and mammalian cellular hosts are described, for example, in Pouwels et al. *Cloning Vectors: A Laboratory Manual*, Elsevier, N.Y., (1985).

In a prokaryotic host cell, such as *E. coli*, an OX40-L polypeptide or analog may include an N-terminal methionine residue to facilitate expression of the recombinant polypeptide in the prokaryotic host cell. The N-terminal Met may be cleaved from the expressed recombinant OX40-L polypeptide. Prokaryotic host cells may be used for expression of OX40-L polypeptides that do not require extensive proteolytic or disulfide processing.

The expression vectors carrying the recombinant OX40-L DNA sequence are transfected or transformed into a substantially homogeneous culture of a suitable host microorganism or mammalian cell line. Transformed host cells are cells which have been transformed or transfected with nucleotide sequences encoding OX40-L polypeptides and express OX40-L polypeptides. Expressed OX40-L polypeptides will be located within the host cell and/or secreted into culture supernatant fluid, depending upon the nature of the host cell and the gene construct inserted into the host cell.

Expression vectors transfected into prokaryotic host cells generally comprise one or more phenotypic selectable markers. A phenotypic selectable marker is, for example, a gene encoding a protein that confers antibiotic resistance or that supplies an autotrophic requirement, and an origin of replication recognized by the host to ensure amplification within the host. Other useful expression vectors for prokaryotic host cells include a selectable marker of bacterial origin derived from commercially available plasmids. This selectable marker can comprise genetic elements of the cloning vector pBR322 (ATCC 37017). pBR322 contains genes for ampicillin and tetracycline resistance and thus provides simple means for identifying transformed cells. The pBR322 "backbone" sections are combined with an appropriate promoter and a OX40-L DNA sequence. Other commercially vectors include, for example, pKK223-3 (Pharmacia Fine Chemicals, Uppsala, Sweden) and pGEM 1 (Promega Biotec, Madison, Wis., U.S.A.).

Promoter sequences are commonly used for recombinant prokaryotic host cell expression vectors. Common promoter sequences include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776) and tac promoter (Maniatis, *Molecular Cloning: A Laboratory Manual*, Cold Spring Harbor Laboratory, p. 412, 1982). A particularly useful prokaryotic host cell expression system employs a phage λ $P_L$ promoter and a cI857ts thermolabile repressor sequence. Plasmid vectors available from the American Type Culture Collection which incorporate derivatives of the λ $P_L$ promoter include plasmid pHUB2 (resident in *E. coli* strain JMB9 (ATCC 37092)) and pPLc28 (resident in *E. coli* RR1 (ATCC 53082)).

OX40-L may be expressed in yeast host cells, preferably from the Saccharomyces genus (e.g., *S. cerevisiae*). Other genera of yeast, such as Pichia or Kluyveromyces, may also be employed. Yeast vectors will often contain an origin of replication sequence from a 2 μ yeast plasmid, an autonomously replicating sequence (ARS), a promoter region, sequences for polyadenylation, and sequences for transcription termination. Preferably, yeast vectors include an origin of replication sequence and selectable marker. Suitable promoter sequences for yeast vectors include promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EPA-73,657.

Yeast vectors can be assembled, for example, using DNA sequences from pBR322 for selection and replication in *E. coli* (Amp$^r$ gene and origin of replication). Other yeast DNA sequences that can be included in a yeast expression construct include a glucose-repressible ADH2 promoter and α-factor secretion leader. The ADH2 promoter has been described by Russell et al. (*J. Biol. Chem.* 258:2674, 1982) and Beier et al. (*Nature* 300:724, 1982). The yeast α-factor leader sequence directs secretion of heterologous polypeptides. The α-factor leader sequence is often inserted between the promoter sequence and the structural gene sequence. See, e.g., Kurjan et al., *Cell* 30:933, 1982 and Bitter et al., *Proc. Natl. Acad. Sci. U.S.A.* 81:5330, 1984. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. U.S.A.* 75:1929, 1978. For example, one can select for Trp$^+$ transformants in a selective medium, wherein the selective medium consists of 0.67% yeast nitrogen base, 0.5% casamino acids, 2% glucose, 10 αg/ml adenine and 20 αg/ml uracil.

Yeast host cells transformed by vectors containing ADH2 promoter sequence may be grown for inducing expression in a "rich" medium. An example of a rich medium is one consisting of 1% yeast extract, 2% peptone, and 1% glucose supplemented with 80 αg/ml adenine and 80 αg/ml uracil. Derepression of the ADH2 promoter occurs when glucose is exhausted from the medium.

Mammalian or insect host cell culture systems could also be employed to express recombinant OX40-L polypeptides. Examples of suitable mammalian host cell lines include the COS-7 line of monkey kidney cells (ATCC CRL 1651; Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines. Suitable mammalian expression vectors include nontranscribed elements such as an origin of replication, a promoter sequence, an enhancer linked to the structural gene, other 5' or 3' flanking nontranscribed sequences, such as ribosome binding sites, a polyadenylation site, splice donor and acceptor sites, and transcriptional termination sequences.

Transcriptional and translational control sequences for mammalian host cell expression vectors may be excised from viral genomes. For example, commonly used mammalian cell promoter sequences and enhancer sequences are derived from Polyoma virus, Adenovirus 2, Simiaii Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a structural gene sequence in a mammalian host cell. Viral early and late promoters are particularly useful because both are easily obtained from a viral genome as a fragment which may also contain a viral origin of replication (Fiers et al., *Nature* 273:113, 1978). Smaller or larger SV40 fragments may also be used, provided the approximately 250 bp sequence extending from the Hind III site toward the Bgl I site located in the SV40 viral origin of replication site is included.

Exemplary mammalian expression vectors can be constructed as disclosed by Okayama and Berg (*Mol. Cell. Biol.* 3:280, 1983). A useful high expression vector, PMLSV N1/N4, described by Cosman et al., *Nature* 312:768, 1984 has been deposited as ATCC 39890. Additional useful mammalian expression vectors are described in EP-A-0367566, and in U.S. Pat. application Ser. No. 07/701,415, filed May 16, 1991, incorporated by reference herein. For expression of a type II protein extracellular region, such as OX40-L, a heterologous signal sequence may be added, such as the signal sequence for interleukin-7 (IL-7) described in U.S. Pat. No. 4,965,195, or the signal sequence for interleukin-2 receptor described in U.S. Pat. No. application 06/626,667 filed on Jul. 2, 1984.

Human or murine OX40-L can be made in membrane-bound form when an intracellular and transmembrane regions are included or in soluble form with only the extracellular domain. CV1/EBNA cells were transfected with a cDNA shown in SEQ ID NO:1in pDC406 to yield transfected cells expressing membrane-bound murine OX40-L.

Purification of Recombinant OX40-L Polypeptides

OX40-L polypeptides may be prepared by culturing transformed host cells under culture conditions necessary to express OX40-L polypeptides. The resulting expressed polypeptides may then be purified from culture media or cell extracts. A OX40-L polypeptide, if desired, may be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred.

Finally, one or more reverse-phase high performance liquid chromatography (RP-HPLC) steps employing hydrophobic RP-HPLC media, (e.g., silica gel having pendant methyl or other aliphatic groups) can be employed to further purify OX40-L. Some or all of the foregoing purification steps, in various combinations, can also be employed to provide a substantially homogeneous recombinant protein.

It is also possible to utilize an affinity column comprising OX40 ligand binding domain to affinity-purify expressed OX40-L polypeptides. OX40-L polypeptides can be removed from an affinity column in a high salt elution buffer and then dialyzed into a lower salt buffer for use.

Recombinant protein produced in bacterial culture is usually isolated by initial disruption of the host cells, centrifugation, extraction from cell pellets if an insoluble polypeptide, or from the supernatant fluid if a soluble polypeptide, followed by one or more concentration, salting-out, ion exchange, affinity purification or size exclusion chromatography steps. Finally, RP-HPLC can be employed for final purification steps. Microbial cells can be disrupted by any convenient method, including freeze-thaw cycling, sonication, mechanical disruption, or use of cell lysing agents.

Transformed yeast host cells are preferably employed to express OX40-L as a secreted polypeptide. This simplifies purification. Secreted recombinant polypeptide from a yeast host cell fermentation can be purified by methods analogous to those disclosed by Urdal et al. (*J. Chromatog.* 296:171, 1984). Urdal et al. describe two sequential, reversed-phase HPLC steps for purification of recombinant human IL-2 on a preparative HPLC column.

Administration of OX40-L Compositions

The present invention provides therapeutic compositions comprising an effective amount of OX40-L in a suitable diluent or carrier and methods of treating mammals using the compositions. For therapeutic use, purified OX40-L or a biologically active analog thereof is administered to a patient, preferably a human, for treatment in a manner appropriate to the indication. Thus, for example, OX40-L pharmaceutical compositions (for example, in the form of a soluble extracellular domain, or a fragment thereof) which is administered to achieve a desired therapeutic effect can be given by bolus injection, continuous infusion, sustained release from implants, or other suitable technique. Typically, a OX40-L therapeutic agent will be administered in the form of a pharmaceutical composition comprising purified 0X40-L polypeptide in conjunction with physiologically acceptable carriers, excipients or diluents. Such carriers will be nontoxic to patients at the dosages and concentrations employed. Ordinarily, the preparation of such compositions entails combining a OX40-L polypeptide with buffers, antioxidants such as ascorbic acid, low molecular weight (less than about 10 residues) polypeptides, proteins, amino acids, carbohydrates including glucose, sucrose or dextrans, chelating agents such as EDTA, glutathione and other stabilizers and excipients. Neutral buffered saline or saline mixed with conspecific serum albumin are exemplary appropriate diluents. OX40-L sense or antisense oligonucleotides may be administered in vivo by administering an effective amount of a vector containing a nucleic acid sequence that encodes and effective antisense or sense oligonucleotide. Additionally, OX40-L sense or antisense oligonucleotides may be administered ex vivo by removing cells containing OX40-L DNA or mRNA from an individual, incorporating an antisense or sense oligonucleotide into the cells using gene transfer techniques, and re-infusing the cells into the individual.

The following examples are intended to illustrate particular embodiments and not limit the scope of the invention.

EXAMPLE 1

This example describes construction of an OX40/Fc DNA construct to express a soluble OX40/Fc fusion protein. The cDNA sequence of the extracellular region or ligand binding domain of complete murine OX40 receptor sequence was obtained using polymerase chain reaction (PCR) techniques, and is based upon the rat sequence published in Mallett et al., *EMBO J.* 9:1063 (1990), supra. Total RNA was obtained from murine T cell clone 7B9 (Mosley et al., *Cell* 59:335; 1989) which had been stimulated with concanavalin A for 26 hours. A first strand cDNA was prepared from oligo dT-primed RNA using a commercially available kit (SuperScript™ cDNA kit; GIBCO/BRL, Gaithersburg, Md.)

A PCR technique (Saiki et al., *Science* 239:487, 1988) was employed using 5' (upstream) and 3' (downstream) oligonucleotide primers to amplify the DNA sequences encoding full length OX40 (SEQ ID Nos:3 and 4, respectively). SEQ ID NO:3 comprises a recognition site for the restriction endonuclease Spe I (nucleotides 4–9) upstream of a sequence encoding the first six (N-terminal) amino acids of OX40 (nucleotides 14–31). SEQ ID NO:4 comprises a recognition site for the restriction endonuclease Spe I (nucleotides 4–9) upstream of a sequence encoding the last five (C-terminal) amino acids of full-length OX40 (nucleotides 10–26).

The PCR conditions were: one cycle at 94° C. for 2 minutes, followed by 42° C. for two minutes; 30 cycles at 72° C. for 1.5 minutes, followed by 94° C. for one minute, then 48° C. for 1 minute; and one cycle at 72° C. for seven minutes. The resulting PCR product comprised the entire coding region of OX40, with Spe I restriction sites on each end.

The PCR product was digested with Spe I, and an approximately 800 bp fragment was isolated by gel filtration, and used in a second round of PCR reaction. The isolated fragment was ligated into Spe I cut plasmid, pBLUESCRIPT SK® (Stratagene Cloning Systems, La Jolla, Calif.), which had been treated with calf intestine alkaline phosphatase (CIAP) to prevent self-ligation. This plasmid was used to PCR an extracellular region of murine OX40; the nucleotide and predicted amino acid sequence of the extracellular domain of mouse OX40 are presented in SEQ ID NOs: 6 and 7.

The oligonucleotide primers used in the PCR reaction were those represented in SEQ ID NO:3 (5') and SEQ ID NO:5 (3'). SEQ ID NO:3 is described above; the oligonucleotide defined by SEQ ID NO:5 deletes the region of murine OX40 that corresponds to the transmembrane region of rat OX40 as described by Mallett et al., and five additional, C-terminal amino acids that are part of the extracellular region. The oligonucleotide represented by SEQ ID NO:5 also includes a Bg II site, and a sequence encoding two amino acids from the N-tenninal of an Fc region of a human IgG$_1$.

The PCR conditions were: five cycles at 94° C. for one minute, followed by 42° C. for one minute, then 72 ° C. for one minute; 25 cycles at 94° C. for one minute, followed by 50° C. for one minute, then 72 ° C. for one minute; and one cycle at 72° C. for seven minutes. An aliquot of the PCR reaction was reamplified in another round of PCR, with the following conditions: 20 cycles at 94° C. for one minute, followed by 55° C. for one minute, then 72° C. for one minute; and one cycle at 72° C. for seven minutes.

The resulting final PCR product was digested with Spe I/Bgl II, and isolated by gel filtration, to yield a fragment of approximately 630 bp. The PCR product was used in a three-way ligation with a Bgl II/Spe I fragment of a DNA encoding a human IgG Fc, into Spe I cut pBLUESCRIPT SK®. After amplification in *E. coli*, the insert encoding the OX40/Fc fusion protein was digested with Sal I/Not I, and cloned into plasmid pDC406 (McMahan et al., *EMBO J.* 10:2821, 1991) which had also been cut with Sal I/Not I. The pDC406 plasmid includes regulatory sequences derived from SV40, human immunodeficiency virus (HIV), and Epstein-Barr virus (EBV), and is also replicable in *E. coli*. The resulting plasmid was designated pDC406/OX40/Fc.

EXAMPLE 2

This example describes construction of an OX40/Fc mutein fusion protein construct to express a soluble OX40/Fc mutein fusion protein for use in detecting cDNA clones encoding an OX40 ligand. pDC406/OX40/Fc was used for site-directed mutagenesis, using a commercially-available kit, Clonetech (Palo Alto, Calif., U.S.A. ) substantially as described by Ray and Nickoloff, *Biotechniques* 13:342 (1992) and Deng and Nickoloff, *Anal. Biochem.* 200:81 (1992). Three amino acid residues in the Fc region were changed (Leu234 to Ala, Leu235 to Glu and Gly237 to Ala, using the amino acid numbering of Canfield and Morrison,*J. Exp. Med.* 173:1,483; 1991).

Briefly, two mutagenic oligonucleotide primers were prepared. The first primer (SEQ ID NO:8) contained the desired mutations, changing the codon CTC (encoding Leu), to GCC (encoding Ala); changing the codon CTG (encoding Leu) to GAG (encoding Glu), and the codon GGA (encoding Gly) to GCG (encoding Ala). The second primer (SEQ ID NO:9) contained a mutation in a unique restriction site, Pvu I. This restriction site is found in the ampicillin resistance gene of pDC406 at position 3542.

The resulting DNA was transformed into a mismatch repair defective *E. coli*strain BMH 71-18 mutS to increase the probability that the two mutations would not be removed by in vivo DNA repair mechanisms, anid would cosegregate during the first round of DNA replication. Transformants were selected using ampicillin, and plasmid DNA prepared. The plasmid DNA was treated with the enzyme Pvu I, to linearize parental molecules and thereby reduce the efficiency of the parental molecules to transform bacteria. Plasmids that contained the mutation were not linearized, and were able to transform bacteria efficiently, allowing facile amplification of the plasmid encoding the OX40/Fc mutein. Following transformation of *E.coli* strain DHI()B, amplified plasmid DNA was prepared. A clone was isolated which contained mutations at the appropriate residues in the Fc portion of the sequence, and which had lost the unique Pvu I site.

The plasmid encoding the resulting mutein was referred to as pDC406/OX40/Fc*. The nucleotide and predicted amino acid sequence of pDC406/OX40/Fc* are shown in SEQ ID NOs:10 and 11; the protein encoded thereby is referred to as OX40/Fc mutein. The resulting OX40/Fc mutein exhibited reduced affinity for immunoglobulin receptors. The mutant amino acids designated 234, 235 and 237 by Canfield and Morrison, supra, correspond to amino acids 225, 226 and 228 , respectively, of SEQ ID NOs: 10 and 11.

PDC406/OX40/Fc* was transfected into the monkey kidney cell line CV-1/EBNA (ATCC CRL 10478). The CV-1/EBNA cell line was derived by transfection of the CV-1cell line with a gene encoding Epstein-Barr virus nuclear antigen-1 (EBNA-1) that constitutively expresses EBNA-1 driven from the human CMV intermediate-early enhancer/promoter. The EBNA-1 gene allows for episomal replication of expression vectors, such as pDC406, that contain the EBV origin of replication.

Once cells expressing the fusion construct were identified, large scale cultures of transfected cells were grown to accumulate supernatant from cells expressing OX40/Fc mutein. The OX40/Fc mutein in supernatant fluid was purified by affinity purification. Briefly, culture supernatant containing the OX40/Fc fusion protein was purified by filtering mammalian cell supernatants (e.g., in a 0.45 μ filter) and applying filtrate to a protein A antibody affinity column (BioRad, Richmond, Calif., U.S.A. ) at 4° C. at a flow rate of approximately 80 ml/hr for a 1.5 cm×12.0 cm column. The column was washed with PBS (phosphate buffered saline) until free protein could not be detected in wash buffer. Bound OX40/Fc mutein was eluted from the column with 50 mM citrate buffer, pH 2.8, and brought to pH 7 with 5 N NaOH. Silver-stained SDS gels of the eluted OX40/Fc mutein showed it to be >90% pure.

EXAMPLE 3

This example describes selection of a cell line putatively expressing membranebound OX40-L. Several cell lines were screened using OX40/Fc mutein prepared according to Example 2, and biotin-labeled goat anti-human IgG antibody (Jackson Labs, Bar Harbor, Me.). Briefly, several different cell lines were analyzed according to standard methodology for flow cytometry. A clonal cell line, S49.1 (ATCC TIB 128 ; a murine T cell lymphoma line) was found to express approximately 1000 molecules of putative OX40-L per cell. The cell line was subjected to several rounds of sorting using flow cytometry, in order to enrich for a population that expressed high levels of the putative OX40-L. Cells from the fourth round of sorting, referred to as OX49.4, were cultured and found to express approximately 15,000 molecules of OX40-L per cell.

EXAMPLE 4

This example describes preparation of a cDNA library for expression cloning of muOX40-L. The cDNA expression library was made essentially as described in U.S. Pat. No. 4,968,607, the disclosure of which is incorporated by reference herein. Briefly, murine lymphoma cells from the line S49.1 (ATCC TIB 128 ) were incubated for 6 hours in 10 ng/ml of the phorbol ester myristic acid (PMA), and RNA was isolated by isothiocyanate extraction and ultracentrifugation as described in Chirgwin et al. Biochem. 18:5294 (1979) and Sambrook et al., *Molecular Cloning: A Laboratory Manual*, Cold Spring Harbor Press, Cold Spring Harbor, N.Y., second ed. (1989).

Poly A⁺ mRNA was isolated by oligo dT cellulose chromatography (Aviv and Leder, *Proc. Natl. Acad. Sci. U.S.A.* 69:1408, 1972) and double stranded cDNA made substantially as described by Gubler et al. *Gene* 25:263, 1983. PolyA⁺ mRNAs were converted to RNA-cDNA hybrids with the enzyme reverse transcriptase using random hexanucleotide primers. The RNA-cDNA hybrids were then converted to double-stranded cDNA fragments using RNaseH in combination with *E.coli* DNA polymerase I. The double-stranded cDNA ends were rendered blunt with Klenow fragment of polymerase I.

The following primers #1 and #2, capable of ligating to a digested Bgl II site, were used to adaptor the cDNA and cloning vector essentially as described in Haymerle et al. *Nucl. Acids Res.* 14:8615, (1986):

1 5'-GATCTTGGAAcGAGAcGAcCTGcT-3' OH SEQ ID No:12

2 5'-AGCAGGTCGTCTCGTTCCAA-3' OH SEQ ID:13

After annealing the primers were ligated to the 5' ends of the blunt-ended cDNAs, and the non-ligated adaptors and complementary strands (primer #2) were removed by gel filtration chromatography at 68° C. This left single strand 24 nucleotide overhangs on the cDNA which were non-self complementary. The same procedure was used to ligate primer #2 to the 5' Bgl II ends of the mammalian expression vector pDC410 (a derivative of pDC406 (McMahan et al. *EMBO J.* 10: 2821, 1991) with a unique Bgl II site and bearing the SV40 T antigen gene) to create 24 nucleotide overhangs complementary to those added to the cDNA. Optimal proportions of vector and cDNA were then ligated with T4 DNA ligase in the presence of T4 polynucleotide kinase. Dialyzed ligation mixtures were introduced into *E. coli* strain DH5α (Bethesda Research Laboratories, *Bethesda Res. Focus* 8(2):9, 1986) by electroporation. Transformants were selected on ampicillin plates.

Plasmid DNA was isolated from pools consisting of approximately 2,000 *E.coli* clones per pool. The isolated DNA was transfected into a sub-confluent layer of CV-1/ EBNA cells (McMahan et al. *EMBO J.* 10:2821, 1991) using DEAE-dextran in chloroquine containing media followed by DMSO shock, substantially according to the procedures described in Luthman et al., *Nucl. Acids Res.* 11:295 (1983) and McCutchan et al., *J. Natl. Cancer Inst.* 41:351 (1986).

CV-1/EBNA cells were maintained in complete medium (Dulbecco's modified Eagles's media containing 10% v/v fetal calf serum, 50U/ml streptomycin, and 2 mM Lglutamine) and were plated to a density of approximately $2 \times 10^5$ cells/well in single-well chambered slides that had been pre-treated with I ml human fibronectin solution (10 µg/ml in PBS) for 30 minutes. After approximately 24 hours growth media was removed from the adherent layer of cells and replaced with 1.5 ml complete media containing 66.6 µM chloroquine sulfate. DNA solution (0.2 ml with 2.0 µg DNA and 0.5 mg/ml DEAE-dextran in complete media plus chloroquine) was added to the cells. The mixture was incubated at 37° C. for 4.5 hours prior to shocking the cells by the addition of complete media containing 10% dimethylsulphoxide for approximately 5 minutes.

EXAMPLE 5

This example describes the screening of the expression library made in Example 4 by slide autoradiography (Gearing et al. *EMBO J* 8:3667,1989) to detect OX40-L expression. OX40/Fc mutein fusion protein made in Example 2 was used in combination with $^{125}$I-labeled anti-human IgG F(ab)$_2$ antibody to detect fusion protein bound to the ligand.

Murine anti-human IgG Fc (F(ab)$_2$ (Jackson Labs, Bar Harbor, Me.) was radioiodinated to a specific activity of $5-15 \times 10^{15}$ cpm/mmol using chloramine-T catalysis and removal of unincorporated $^{125}$-I by gel filtration as follows. A chloramine-T solution of 2 mg/ml was freshly prepared in 0.05M sodium phosphate buffer (pH 7.2) and 15 µl added to each of 2 microfuge tubes containing 5 µg of the anti-human IgG Fc (F(ab)$_2$ fragment in approximately 5 µl PBS, followed by 2 millicuries of Na $^{125}$I (added in 20 µl of 0.05M sodium phosphate buffer (pH 7.2). The mixture was incubated for 30 minutes at room temperature and then applied to a Sephadex G-25 column that had been packed according to manufacturer's instructions, and washed with 5 volumes of PBS. The radiolabeled antihuman IgG Fc (F(ab)$_2$ was eluted from the column in approximately 100 µl fractions, the peak fractions pooled, and diluted to 4 ml in binding medium that lacked non-fat dry milk (RPMI 1640 containing 25 mg/ml bovine serum albumin (BSA), 2 mg/ml sodium azide, 20 mM HEPES pH 7.2). Level of incorporation was determined by quantitating the cpm in a measured aliquot and in a trichloroacetic acid (TCA) precipitate of the aliquot with a gamma counter. The labeled protein was $\geq 95\%$ TCA precipitable, indicating that the $^{125}$I was covalently bound to the protein.

CV-1/EBNA cell monolayers were transfected with DNA from cDNA library pools on slides as in Example 3 and incubated 48–72 hours to allow OX40-L expression. The cell layers were washed once with binding medium (RPMI 1640 containing 25 mg/ml bovine serum albumin (BSA), 2 mg/ml sodium azide, 20 mM HEPES pH7.2, and 50 mg/ml nonfat dry milk) that contained reagents to block binding to cellular Fc receptors (20% v/v complement-inactivated calf serum and 25 mg/ml monoclonal anti-murine Fc receptor antibody 2.4G2 (ATCC HB 197)). The cells were then incubated in this medium containing 1 µg/ml OX40/Fc mutein fusion protein for 1 hour at room temperature.

After removal of the OX40/Fc-containing medium, the cells were washed 2 times in binding medium, then incubated for 30 minutes at room temperature in binding medium containing approximately $2 \times 10^{-9}$M $^{125}$I-munine anti-human Fc (F(ab)$_2$ fragment labeled as described above. The cells were then washed 3 times with binding medium, 2 times with PBS, and fixed by incubation for 30 minutes at room temperature in 1 ml 2.5% glutaraldehyde in PBS.

Autoradiography was then performed by dipping the slides in Kodak GTNB-2 photographic emulsion (6×dilution in water) and exposure in the dark for 3–4 days at room temperature. The slides were developed for 4 minutes in Kodak GBX developer (40 g/500 ml water), rinsed for 30 seconds in water, and fixed in Kodak rapid fixer for 4 minutes. Slides were viewed at 25–40×magnification by microscope and cells expressing OX40-L were detected by the presence of dark autoradiographic silver grains.

Using slide audioradiography, approximately 500,000 cDNAs were screened as pools of approximately 2000 to yield 4 pools positive for OX40/Fc mutein binding. An OX40-L cDNA was then isolated from one pool, #198, as follows. *E. coli*cells from #198 were plated on growth medium with ampicillin to generate 25 smaller sub-pools of approximately 250, and DNA was isolated from the subpools.

Each sub-pool was transfected into CV-1/EBNA monolayers, and the monolayers subjected to slide autoradiography as above, with the exception that prior to dipping in photographic emulsion the slides were also exposed on a Phosphoimager (Molecular Dynamics) overnight to aid detection of sub-pools that expressed OX40-L. Cells from individual clones of one positive subpool were picked into liquid medium in a row and column format in a microtiter plate, followed by incubation at 37° C. to allow growth. 100 µl aliquots were removed from the cultures and pooled for members of a row or column. DNAs were prepared from the row and column pools, and transfected into CV-1/EBNA cells on slides substantially as described previously; slide autoradiography was performed on the transfected cells as described above. One row and one column were positive, and defined a single clone, #198-13-33 (#33), containing an OX40-L cDNA. The cDNA insert in clone #33 was 1476 bp as determined by dideoxynucleotide sequencing.

A second OX40-L cDNA clone (#69-9-2) was isolated from positive pool #69 by generating positive sub-pools as described above and screening colonies from the subpools by colony hybridization (Grunstein and Hogness, *Proc. Natl. Acad. Sci. U.S.A.* 72:3961, 1975) with a radioactive OX40-L probe, generated from clone #33 by polymerase chain reaction (Saiki et al *Science* 239:487, 1988) in the presence of $^{32}\alpha$-P-dCTP. The cDNA insert in clone #69-9-2 was extended by 110 bp in the 5' region of the OX40-L cDNA as compared to clone #33, for a total length of was 1586 bp as determined by dideoxynucleotide sequencing. The complete nucleotide and the amino acid coding region for OX40-L derived from it are depicted in SEQ ID NOs:1 and 2, respectively. The coding region for clone #69-9-2 is predicted to begin with nucleotide 148, extending to a stop codon (nucleotides 742–744). Clone #69-9-2 exhibits an open reading frame of 122 bases 5' to the putative intitiator methionine (nucleotides 26–147 of SEQ ID NO:1).

EXAMPLE 6

This example describes the screening for OX40-L cDNA clones with extended 5' ends compared to clone #69-9-2 by first generating OX40-L single stranded cDNAs, and then using a 5' anchored PCR technique substantially as described by Loh et al *Science* 243:217, 1989.

Briefly, starting with RNA containing OX40-L transcript, such as poly A+ RNA isolated from S49.1 cells, reverse transcriptase is used to generate cDNA/RNA hybrids with a primer specific for OX40-L mRNA and complementary to the 3' non-coding region of the OX40-L coding strand. After removal of RNA, the DNA strand is extended by incubating with terminal deoxyribonucleotidyl transferase in the presence of a single deoxynucleotide triphosphate such as dATP. PCR is then initiated to amplify these cDNAs using primers specific for the cDNA strand. In one embodiment, a primer consisting of poly dT and, for purposes of cloning, a 17-mer oligonucleotide including a Not I site at its 5' end is used to prime a strand complementary to the cDNA. This double-stranded DNA product is then amplified by PCR using both the dT containing primer and an excess of a shorter oligonucleotide primer consisting of the non-poly dT bases in combination with a third primer containing a Not I site and bases complementary to the stop codon and the 3' end of the OX40-L coding region.

The amplified product is digested with Not I restriction enzyme and cloned into a Not I digested *E.coli* cloning vector, such as pBluescript SK®. Clones containing an OX40-L cDNA insert are detected by filter hybridization with a oligonucleotide complementary to the 5' end of the OX40-L coding region that was labeled with $^{32}$P by the enzyme T4 polynucleotide kinase (Sambrook et al. *Molecular Cloning: A Laboratory Manual*, Cold Spring Harbor Press, Cold Spring Harbor, N.Y. second ed. (1989)).

A number of techniques may then be used to detect cDNAs with 5' extensions as compared to clone #69-9-2 . In one embodiment, an oligonucleotide primer complementary to the 5' end of the coding region is used, together with an oligonucleotide primer complementary to vector sequences adjacent to the cDNA insert, to again perform anchored PCR so that the 5' region of the cDNA clones is amplified. The products of the PCR reactions are examined by gel electrophoresis and their length compared with a similarly derived amplification product from clone #69-9-2 . The cDNA inserts for those clones giving longer 5' PCR product are then sequenced in their entirety by standard dideoxynucleotide sequencing techniques to determine if a longer OX40-L polypeptide is encoded by the cDNAs.

EXAMPLE 7

This example describes the bioaffinity immunoprecipitation of OX40-L from cells expressing OX40-L. OX49.4 cells, or PMA-stimulated S49.1 cells, were surface labeled with Biotin X-NHS. Briefly, cells were washed with phosphate-buffered saline (PBS), and treated with 100 µg biotin-X-NHS (CalBiochem, San Diego, Calif., U.S.A.) per $10^7$ cells, at pH 7.4 for 30 minutes. The treated cells were then washed with PBS to remove the excess unconjugated biotin, and lysed with 1% TritonX-100/300 Kallikrein units per ml aprotinin-A/5 mM EGTA.

Lysates were incubated with 10 µg/ml OX40/Fc mutein prepared as described in Example 2 (or a control, CD40/Fc protein) for at least two hours at 4° C., with intermittent agitation, to allow the receptor and ligand to form a matrix. In some experiments, the incubation length was up to about 16 hours. Protein-A/G agarose (Pierce, Rockford, Ill.; U.S.A.) was added, and the lysate mixture was incubated one hour at 4° C. to form a precipitable protein A/G-Fc-receptor-ligand matrix.

The precipitable matrix was pelleted by centrifugation, washed extensively in 10 mM HEPES, 0.5% NP-40, and PBS, and resuspended in Laemmili reducing sample buffer. Samples of the precipitable matrix were solubilized by boiling, added to 4–20% gradient acrylamide gels, and electrophoresed under reducing conditions. Bioaffinity immunoprecipitation of labeled OX49.4 or PMA-stimulated S49.1 cells with OX40/Fc mutein resulted in the identification of an abundant, distinct, putative OX40-L protein of approximately 30 Kd in the OX49.4 cells, and a lesser amount of the same Mr protein from the stimulated S49.1 cells, that correlated with surface expression of OX40-L. This protein was not observed in samples that had been incubated with the control CD40/Fc protein.

EXAMPLE 8

This example illustrates T cell proliferative activity of membrane-bound murine OX40-L for murine (mouse and rat) cells. Lymphoid organs were harvested aseptically and cell suspensions were prepared as described (Fanslow et al., *J. Immunol.* 147:535; 1991). Mouse T cells were isolated from spleens of C57B1/6 mice and purified by incubating with monoclonal antibodies against CD11b (Mac-1; Springer et al., *Eur. J. Immunol.* 9:301; 1979) and class II MHC (25-9-17; Ozato et al., *J. Immunol.* 126:317;1981) for 30 minutes at 4° C. loading the incubated cell preparations onto a T cell purification column (Pierce, Rockford, Ill., U.S.A.), and eluting the T cells according to the manufacturer's instrucitons. Rat T cells were purified from the spleens of Lewis rats by negative selection using sheep anti-rat IgG coated magnetic beads (Dynal, Bioproducts for Science, Indianapolis, Ind., U.S.A.) to remove the rat B cells and monocytes.

T cell proliferation assays were set up in round- or flat-bottomed 96-well plates using 0.5 to $1.5\times10^5$ cells per well. Mouse T cells were cultured in the presence of a sub-optimal level (0.5 μg/ml) of concanvalin A (Con A; Sigma, St. Louis, Mo., U.S.A.); rat T cells were cultured in the presence of sub-optimal levels of phytohemagglutinin (PHA; Difco, Detroit, Mich., U.S.A.), either 0.5% w/v or 1.0% w/v PHA. Both rat and mouse T cell cultures also included CV-1/EBNA cells transfected either with murine OX40-L cDNA or vector alone (HAVEO), prepared as described in Example 5, and fixed at two days post-transfection with 1% paraformaldehyde for five minutes at 25° C. The T cells were pulsed with 1 μCi/well of tritiated thymidine (25 Ci/nmole, Amersham, Arlington Heights, Ill., U.S.A.) for the final eighteen hours of a three day culture. T cells were harvested onto glass fiber discs with an automated cell harvester and incorporated radioactivity was measured using a Matrix 96 beta counter (Packard-Bell, Meridian, Conn., U.S.A.).

Figure 2:
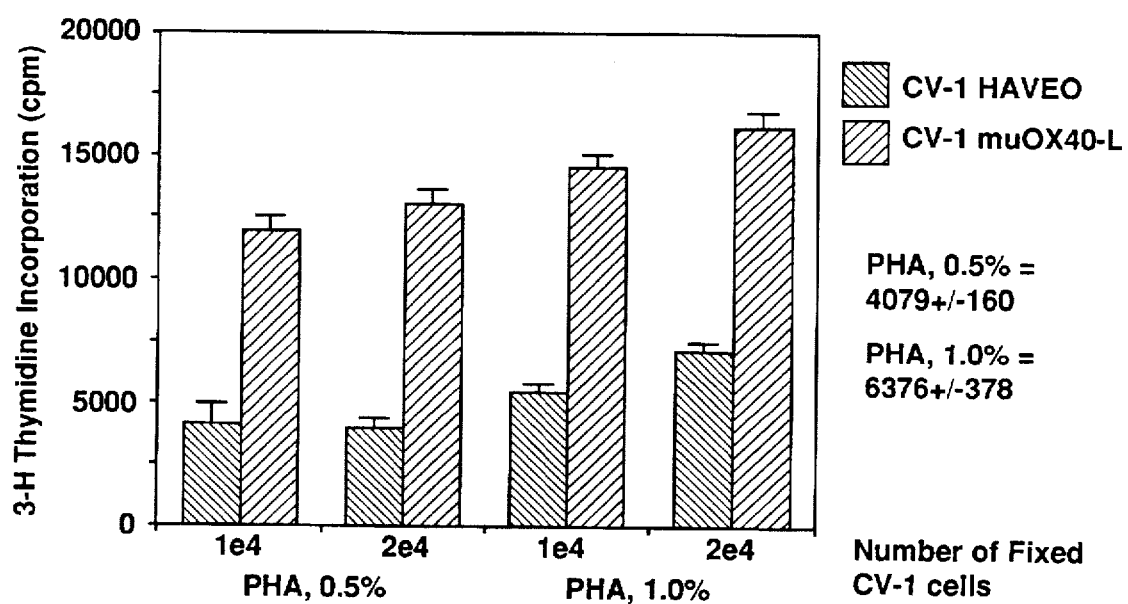
FIG. 2 illustrates the effect of fixed CV-1/EBNA cells transfected with an expression vector encoding mouse OX40-L versus fixed CV-1/EBNA cells transfected with vector alone on the proliferation of rat T cells in the presence of suboptimal levels of mitogen (Phytohemagglutinin at either 0.5% w/v or 1.0% w/v).

FIG. 1 shows a comparison of mouse T cell proliferation by CV1 EBNA cells transfected with vector alone (HAVEO) or with murine OX40-L cDNA in HAVEO vector. These data show that membrane-bound OX40-L stimulates mouse T cell proliferation in the presence of a sub-optimal level of a co-mitogen. FIG. 2 shows a comparison of rat T cell proliferation by CV1 EBNA cells transfected with vector alone (HAVEO) or with murine OX40-L cDNA in HAVEO vector. These data show that membrane-bound OX40-L stimulates rat T cell proliferation in the presence of sub-optimal levels of a co-mitogen. Accordingly, membrane-bound OX40-L co-stimulates proliferation of murine T cells.

EXAMPLE 9

This example illustrates the ability of membrane-bound murine OX40-L to stimulate cytokine secretion from murine T cells. Purified lymph node T cells from C57B1/6 mice (a mixture of both CD4+ and CD8+ cells; approximately $1\times10^5$ cells/well) were incubated in microtiter wells left untreated (medium) or coated with 0.2 μg/ml anti-TCR:αβ(H57-597; Kubo et al., *J. Immunol.* 142:2736; 1989). In addition to the lymphocytes, wells contained either no addition (TCR) or CV-1/EBNA cells ($10^4$/well) transfected with murine OX40-L cDNA or vector alone (HAVEO), as described previously, or the wells also contained IL-2 (5 ng/ml: Immunex, Seattle, Wash., U.S.A.) or anti-CD28 ascites (37.5; Gross et al., *J. Immunol.* 149:380; 1992) diluted 1:1000. Culture supernatant was harvested from these cultures after 48 hours, and analyzed for the presence of IL-2 and/or IL-4. IL-2 and IL-4 levels were measured by bioassay usng using the IL-2 and IL-4 dependent cell lines CTLL-2 (Gillis et al., *J. Immunol.* 120:2027; 1978) and CT.4S (Hu-Li et al., *J. Immunol.* 142:800; 1989). Proliferation of the CTLL-2 and CT.4S cells was measured after 36 hours of culture with the supernatant harvested from the T cell cultures, using a standard $^3$H-thymidine incorporation assay.

Figure 3:
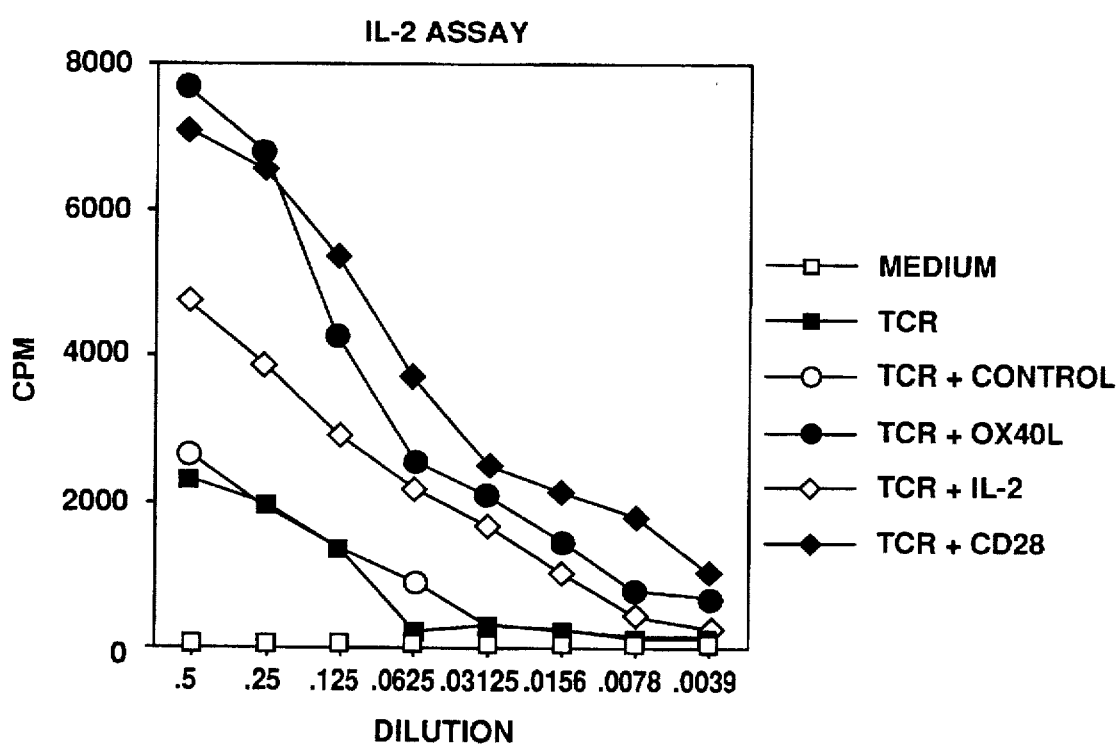
FIG. 3 illustrates the effect of fixed CV-1/EBNA cells transfected with an expression vector encoding mouse OX40-L versus fixed CV-1/EBNA cells transfected with vector alone on the secretion of IL-2 by mouse T cells.
Figure 4:
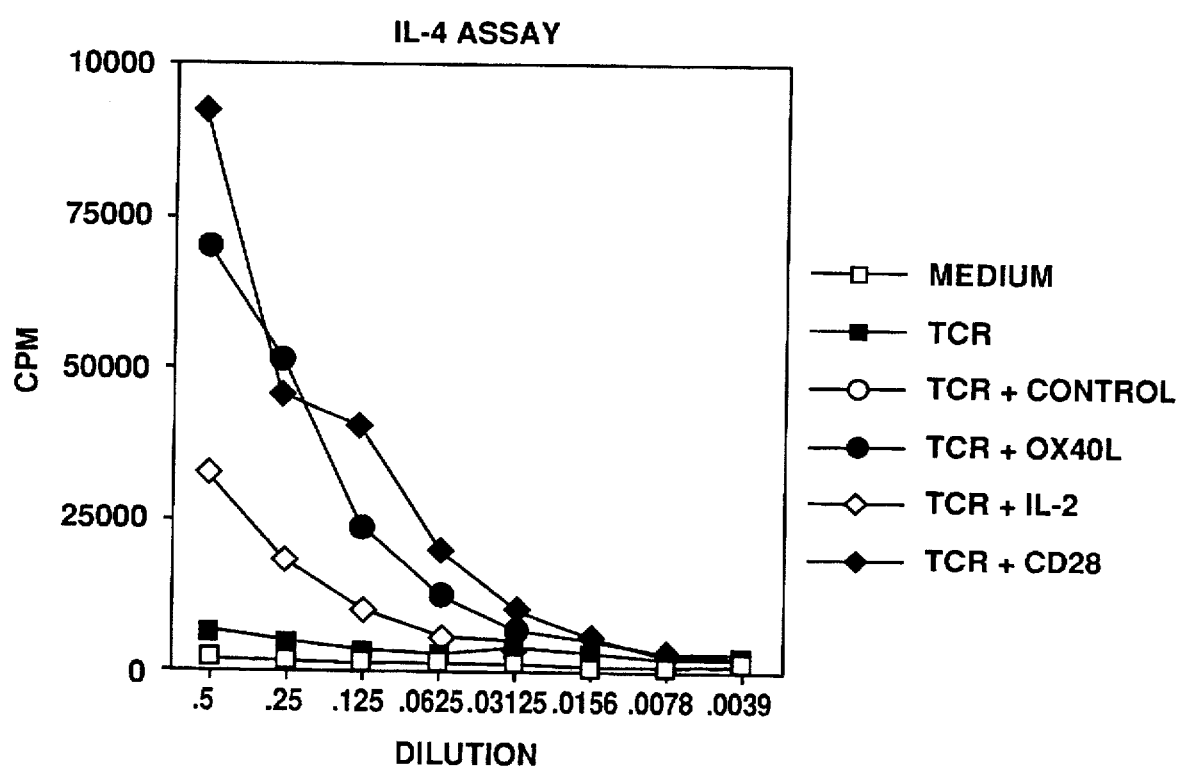
FIG. 4 illustrates the effect of fixed CV-1/EBNA cells transfected with an expression vector encoding mouse OX40-L versus fixed CV-1/EBNA cells transfected with vector alone on the secretion of IL-4 by mouse T cells.

FIG. 3 illustrates the proliferation of CTLL-2 cells, an IL-2 -dependent cell line, in response to the harvested supernatants. FIG. 4 shows the proliferation of CT.4S cells, an IL-4 -dependent cell line, in response to the harvested supernatants. Taken together, the results demonstrate that OX40-L is a potent co-stimulus for IL-2 and IL-4 production in T cells. Further, the ability of OX40-L to induce levels of IL-2 and IL-4 similar to those induced in the presence of anti-CD28 suggests that OX40-L provides an extremely potent co-stimulatory signal.

EXAMPLE 10

This example illustrates the preparation of monoclonal antibodies to OX40-L. OX40-L is expressed in mammalian cells such as COS-7 or CV-1/EBNA cells, and purified using OX40/Fc affinity purification. Purified OX40-L, fragments thereof (such as the extracellular domain), synthetic peptides, or cells over-expressing OX40-L can be used as immunogens to generate monoclonal antibodies against OX40-L using conventional techniques, for example, those techniques described in U.S. Pat. No. 4,411,993. Briefly, mice are immunized with OX40-L as an immunogen emulsified in complete Freund's adjuvant, and injected in amounts ranging from 10–100 μg subcutaneously or intraperitoneally. Ten to twelve days later, the immunized animals are boosted with additional OX40-L emulsified in incomplete Freund's adjuvant. Mice are periodically boosted thereafter on a weekly to bi-weekly immunization schedule. Serum samples are periodically taken by retro-orbital bleeding or tail-tip excision for testing by dot blot assay, ELISA (Enzyme-Linked Immunosorbent Assay), or inhibition of OX40-L binding, for OX40-L antibodies.

Following detection of an appropriate antibody titer, positive animals are provided one last intravenous injection of OX40-L in saline. Three to four days later, the animals are sacrificed, spleen cells harvested, and spleen cells are fused to a murine myeloma cell line (e.g., NS1 or preferably Ag 8.653 [ATCC CRL 1580]). Fusions generate hybridoma cells, which are plated in multiple microtiter plates in a HAT (hypoxanthine, aminopterin and thymidine) selective medium to inhibit proliferation of non-fused cells, myeloma hybrids, and spleen cell hybrids.

The hybridoma cells are screened by ELISA for reactivity against purified OX40-L by adaptations of the techniques disclosed in Engvall et al., *Immunochem.* 8:871, 1971 and in U.S. Pat. No. 4,703,004. A preferred screening technique is the antibody capture technique described by Beckman et al., *J. Immunol.* 144:4212 (1990). Positive hybridoma cells can be injected intraperitoneally into syngeneic BALB/c mice to produce ascites containing high concentrations of anti-OX40-L monoclonal antibodies. Alternatively, hybridoma cells can be grown in vitro in flasks or roller bottles by various techniques. Monoclonal antibodies produced in mouse ascites can be purified by ammonium sulfate precipitation, followed by gel exclusion chromatography. Alternatively, affinity chromatography based upon binding of antibody to protein A or protein G can also be used, as can affinity chromatography based upon binding to OX40-L.

---

What is claimed is:

1. A purified OX40-ligand selected from the group consisting of:

(a) a polypeptide comprising amino acids 1 through 198, inclusive, of the sequence set forth in SEQ ID NO:2;

(b) a polypeptide comprising amino acids 49 through 198, inclusive, of the sequence set forth in SEQ ID NO:2;

(c) a polypeptide comprising a sequence beginning with an amino acid in the sequence between amino acid 49 and amino acid 69, inclusive, through and including an amino acid in the sequence between amino acid 164 and amino acid 198, inclusive, of the sequence set forth in SEQ ID NO:2; and (d) a polypeptide which differs from that of (a), (b) or (c) by changes in the amino acid sequence selected from the group consisting of inactivated N-linked glycosylation sites, substituted or deleted cysteine residues, and a peptide added to facilitate purification, wherein the OX40 ligand polypeptide binds OX40.

2. A purified OX40-ligand polypeptide comprising amino acids 49 through 198 of the sequence set forth in SEQ ID NO:2.

3. A composition comprising an OX40-ligand according to claim 2, and a diluent or carrier.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 1633 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i i ) IMMEDIATE SOURCE:
        ( B ) CLONE: MUSOX40-L ( i x ) FEATURE:
        ( A ) NAME/KEY: CDS
        ( B ) LOCATION: 148..744

( x i ) SEQUENCE DESCRIPTION: SEQ ID NO:1:

```
AGATCTTGGA ACGAGACGAC CTGCTGGGAC CTTTATCTTC TGACCCGCAG GCTTGACTTT      60

GCCCTTATTG GCTCCTTTGT GGTGAAGAGC AGTCTTCCCC CAGGTTCCCC GCCACAGCTG     120

TATCTCCTCT GCACCCCGAC TGCAGAG ATG GAA GGG GAA GGG GTT CAA CCC        171
                              Met Glu Gly Glu Gly Val Gln Pro
                                1               5

CTG GAT GAG AAT CTG GAA AAC GGA TCA AGG CCA AGA TTC AAG TGG AAG      219
Leu Asp Glu Asn Leu Glu Asn Gly Ser Arg Pro Arg Phe Lys Trp Lys
         10              15                  20

AAG ACG CTA AGG CTG GTG GTC TCT GGG ATC AAG GGA GCA GGG ATG CTT      267
Lys Thr Leu Arg Leu Val Val Ser Gly Ile Lys Gly Ala Gly Met Leu
 25              30              35                  40

CTG TGC TTC ATC TAT GTC TGC CTG CAA CTC TCT TCC TCT CCG GCA AAG      315
Leu Cys Phe Ile Tyr Val Cys Leu Gln Leu Ser Ser Ser Pro Ala Lys
                 45              50                  55

GAC CCT CCA ATC CAA AGA CTC AGA GGA GCA GTT ACC AGA TGT GAG GAT      363
Asp Pro Pro Ile Gln Arg Leu Arg Gly Ala Val Thr Arg Cys Glu Asp
             60              65                  70

GGG CAA CTA TTC ATC AGC TCA TAC AAG AAT GAG TAT CAA ACT ATG GAG      411
Gly Gln Leu Phe Ile Ser Ser Tyr Lys Asn Glu Tyr Gln Thr Met Glu
         75              80              85

GTG CAG AAC AAT TCG GTT GTC ATC AAG TGT GAT GGG CTT TAT ATC ATC      459
Val Gln Asn Asn Ser Val Val Ile Lys Cys Asp Gly Leu Tyr Ile Ile
         90              95              100

TAC CTG AAG GGC TCC TTT TTC CAG GAG GTC AAG ATT GAC CTT CAT TTC      507
Tyr Leu Lys Gly Ser Phe Phe Gln Glu Val Lys Ile Asp Leu His Phe
105             110                 115                 120

CGG GAG GAT CAT AAT CCC ATC TCT ATT CCA ATG CTG AAC GAT GGT CGA      555
Arg Glu Asp His Asn Pro Ile Ser Ile Pro Met Leu Asn Asp Gly Arg
                125                 130                 135

AGG ATT GTC TTC ACT GTG GTG GCC TCT TTG GCT TTC AAA GAT AAA GTT      603
Arg Ile Val Phe Thr Val Val Ala Ser Leu Ala Phe Lys Asp Lys Val
            140                 145                 150

TAC CTG ACT GTA AAT GCT CCT GAT ACT CTC TGC GAA CAC CTC CAG ATA      651
Tyr Leu Thr Val Asn Ala Pro Asp Thr Leu Cys Glu His Leu Gln Ile
            155                 160                 165

AAT GAT GGG GAG CTG ATT GTT GTC CAG CTA ACG CCT GGA TAC TGT GCT      699
Asn Asp Gly Glu Leu Ile Val Val Gln Leu Thr Pro Gly Tyr Cys Ala
170                 175                 180

CCT GAA GGA TCT TAC CAC AGC ACT GTG AAC CAA GTA CCA CTG TGAATTCCAC   751
Pro Glu Gly Ser Tyr His Ser Thr Val Asn Gln Val Pro Leu
185                 190                 195

TCTGAGGGTG GACGGGACAC AGGTTCTTTC TCGAGAGAGA TGAGTGCATC CTGCTCATGA    811
```

-continued

```
GATGTGACTG AATGCAGAGC CTACCCTACT TCCTCACTCA GGGATATTTA AATCATGTCT    871

TACATAACAG TTGACCTCTC ATTCCAGGA TTGCCTTGAG CCTGCTAAGA GCTGTTCTGG    931

GAATGAAAAA AAAATAAATG TCTCTTCAAG ACACATTGCT TCTGTCGGTC AGAAGCTCAT    991

CGTAATAAAC ATCTGCCACT GAAATGGCG CTTGATTGCT ATCTTCTAGA ATTTGATGT    1051

TGTCAAAAGA AAGCAAAACA TGGAAAGGGT GGTGTCCACC AGCCAGTAGG AGCTGGAGTG    1111

CTCTCTCCAG GTTAAGGTGA TAGAAGTTTA CATGTTGCCT AAAACTGTCT CTCATCTCAT    1171

GGGGGGCTTG GAAAGAAGAT TACCCCGTGG AAAGCAGGAC TTGAAGATGA CTGTTTAAGC    1231

AACAAGGTGC ACTCTTTTCC TGGCCCCTGA ATACACATAA AAGACAACTT CCTTCAAAGA    1291

ACTACCTAGG GACTATGATA CCCACCAAAG AACCACGTCA GCGATGCAAA GAAAACCAGG    1351

AGAGCTTTGT TTATTTTGCA GAGTATACGA GAGATTTTA CCCTGAGGGC TATTTTTATT    1411

ATACAGAATG ATAGTGAACT GGATGTCTCA GGATAAAGGC CAAGAAGGAT TTTTCACAGT    1471

CTGAGCAAGA CTGTTTTTGT AGGTTTCTCT CTCCAAAACT TTAGGTAAA TTTTTGATAA    1531

TTTTTAAATT TTTATATTTT TGGACCATTT TCAATAGAAG ATTGAAACAT TTCCAGATGG    1591

TTTCATATCC CCACAAGAGC AGGTCGTCTC GTTCCAAGAT CT                       1633
```

( 2 ) INFORMATION FOR SEQ ID NO:2:

( i ) SEQUENCE CHARACTERISTICS:
        ( A ) LENGTH: 198 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Glu Gly Glu Gly Val Gln Pro Leu Asp Glu Asn Leu Glu Asn Gly
 1               5                  10                  15

Ser Arg Pro Arg Phe Lys Trp Lys Lys Thr Leu Arg Leu Val Val Ser
            20                  25                  30

Gly Ile Lys Gly Ala Gly Met Leu Leu Cys Phe Ile Tyr Val Cys Leu
        35                  40                  45

Gln Leu Ser Ser Ser Pro Ala Lys Asp Pro Pro Ile Gln Arg Leu Arg
    50                  55                  60

Gly Ala Val Thr Arg Cys Glu Asp Gly Gln Leu Phe Ile Ser Ser Tyr
65                  70                  75                  80

Lys Asn Glu Tyr Gln Thr Met Glu Val Gln Asn Asn Ser Val Val Ile
                85                  90                  95

Lys Cys Asp Gly Leu Tyr Ile Ile Tyr Leu Lys Gly Ser Phe Phe Gln
            100                 105                 110

Glu Val Lys Ile Asp Leu His Phe Arg Glu Asp His Asn Pro Ile Ser
        115                 120                 125

Ile Pro Met Leu Asn Asp Gly Arg Arg Ile Val Phe Thr Val Val Ala
    130                 135                 140

Ser Leu Ala Phe Lys Asp Lys Val Tyr Leu Thr Val Asn Ala Pro Asp
145                 150                 155                 160

Thr Leu Cys Glu His Leu Gln Ile Asn Asp Gly Glu Leu Ile Val Val
                165                 170                 175

Gln Leu Thr Pro Gly Tyr Cys Ala Pro Glu Gly Ser Tyr His Ser Thr
            180                 185                 190

Val Asn Gln Val Pro Leu
        195
```

( 2 ) INFORMATION FOR SEQ ID NO:3:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i i ) IMMEDIATE SOURCE:
        ( B ) CLONE: Oligo 6142

( x i ) SEQUENCE DESCRIPTION: SEQ ID NO:3:

GTCACTAGTC ACCATGTATG TGTGGGTTCA G        31

( 2 ) INFORMATION FOR SEQ ID NO:4:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( v i i ) IMMEDIATE SOURCE:
        ( B ) CLONE: Oligo 6163

( x i ) SEQUENCE DESCRIPTION: SEQ ID NO:4:

CAGACTAGTT CAGATCTTGG CTAGAG        26

( 2 ) INFORMATION FOR SEQ ID NO:5:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( v i i ) IMMEDIATE SOURCE:
        ( B ) CLONE: Oligo 6162

( x i ) SEQUENCE DESCRIPTION: SEQ ID NO:5:

CACAAGATCT GGGCTCCACC AAGGTGGGTG TAG        33

( 2 ) INFORMATION FOR SEQ ID NO:6:

( i ) SEQUENCE CHARACTERISTICS:
        ( A ) LENGTH: 618 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO -continued (vii) IMMEDIATE SOURCE:
  (B) CLONE: MOUSE OX40

(ix) FEATURE:
  (A) NAME/KEY: CDS
  (B) LOCATION: 1..618

(xi) SEQUENCE DESCRIPTION: SEQ ID NO:6:

| ATG | TAT | GTG | TGG | GTT | CAG | CAG | CCC | ACA | GCC | CTT | CTG | CTG | CTG | GGA | CTC | 48 |
| Met | Tyr | Val | Trp | Val | Gln | Gln | Pro | Thr | Ala | Leu | Leu | Leu | Leu | Gly | Leu | |
| 1 | | | | 5 | | | | | 10 | | | | | 15 | | |

| ACA | CTT | GGA | GTT | ACA | GCA | AGG | CGG | CTC | AAC | TGT | GTT | AAA | CAT | ACC | TAC | 96 |
| Thr | Leu | Gly | Val | Thr | Ala | Arg | Arg | Leu | Asn | Cys | Val | Lys | His | Thr | Tyr | |
| | | | 20 | | | | | 25 | | | | | 30 | | | |

| CCC | AGT | GGT | CAC | AAG | TGC | TGT | CGT | GAG | TGC | CAG | CCA | GGC | CAT | GGT | ATG | 144 |
| Pro | Ser | Gly | His | Lys | Cys | Cys | Arg | Glu | Cys | Gln | Pro | Gly | His | Gly | Met | |
| | | 35 | | | | | 40 | | | | | 45 | | | | |

| GTG | AAC | CGC | TGT | GAT | CAT | ACC | AGG | GAT | ACT | CTA | TGT | CAT | CCG | TGT | GAG | 192 |
| Val | Asn | Arg | Cys | Asp | His | Thr | Arg | Asp | Thr | Leu | Cys | His | Pro | Cys | Glu | |
| | 50 | | | | | 55 | | | | | 60 | | | | | |

| ACT | GGC | TTC | TAC | AAT | GAA | GCT | GTC | AAT | TAT | GAT | ACC | TGC | AAG | CAG | TGT | 240 |
| Thr | Gly | Phe | Tyr | Asn | Glu | Ala | Val | Asn | Tyr | Asp | Thr | Cys | Lys | Gln | Cys | |
| 65 | | | | | 70 | | | | | 75 | | | | | 80 | |

| ACA | CAG | TGC | AAC | CAT | CGA | AGT | GGA | AGT | GAA | CTC | AAG | CAG | AAT | TGC | ACA | 288 |
| Thr | Gln | Cys | Asn | His | Arg | Ser | Gly | Ser | Glu | Leu | Lys | Gln | Asn | Cys | Thr | |
| | | | | 85 | | | | | 90 | | | | | 95 | | |

| CCT | ACT | CAG | GAT | ACT | GTC | TGC | AGA | TGT | AGA | CCA | GGC | ACC | CAA | CCT | CGG | 336 |
| Pro | Thr | Gln | Asp | Thr | Val | Cys | Arg | Cys | Arg | Pro | Gly | Thr | Gln | Pro | Arg | |
| | | | 100 | | | | | 105 | | | | | 110 | | | |

| CAG | GAC | AGC | GGC | TAC | AAG | CTT | GGA | GTT | GAC | TGT | GTT | CCC | TGC | CCT | CCT | 384 |
| Gln | Asp | Ser | Gly | Tyr | Lys | Leu | Gly | Val | Asp | Cys | Val | Pro | Cys | Pro | Pro | |
| | | 115 | | | | | 120 | | | | | 125 | | | | |

| GGC | CAC | TTT | TCT | CCA | GGC | AAC | AAC | CAG | GCC | TGC | AAG | CCC | TGG | ACC | AAT | 432 |
| Gly | His | Phe | Ser | Pro | Gly | Asn | Asn | Gln | Ala | Cys | Lys | Pro | Trp | Thr | Asn | |
| | 130 | | | | | 135 | | | | | 140 | | | | | |

| TGT | ACC | TTA | TCT | GGA | AAG | CAG | ACC | CGC | CAC | CCA | GCC | AGT | GAC | AGC | TTG | 480 |
| Cys | Thr | Leu | Ser | Gly | Lys | Gln | Thr | Arg | His | Pro | Ala | Ser | Asp | Ser | Leu | |
| 145 | | | | | 150 | | | | | 155 | | | | | 160 | |

| GAC | GCA | GTC | TGT | GAG | GAC | AGA | AGC | CTC | CTG | GCC | ACA | CTG | CTC | TGG | GAG | 528 |
| Asp | Ala | Val | Cys | Glu | Asp | Arg | Ser | Leu | Leu | Ala | Thr | Leu | Leu | Trp | Glu | |
| | | | | 165 | | | | | 170 | | | | | 175 | | |

| ACC | CAG | CGC | CCT | ACA | TTC | AGG | CCA | ACC | ACT | GTC | CAA | TCC | ACC | ACA | GTC | 576 |
| Thr | Gln | Arg | Pro | Thr | Phe | Arg | Pro | Thr | Thr | Val | Gln | Ser | Thr | Thr | Val | |
| | | | 180 | | | | | 185 | | | | | 190 | | | |

| TGG | CCC | AGG | ACT | TCT | GAG | TTG | CCC | TCT | ACA | CCC | ACC | TTG | GTG | | | 618 |
| Trp | Pro | Arg | Thr | Ser | Glu | Leu | Pro | Ser | Thr | Pro | Thr | Leu | Val | | | |
| | | 195 | | | | | 200 | | | | | 205 | | | | |

(2) INFORMATION FOR SEQ ID NO:7:

(i) SEQUENCE CHARACTERISTICS:
    (A) LENGTH: 206 amino acids
    (B) TYPE: amino acid
    (D) TOPOLOGY: linear (ii) MOLECULE TYPE: protein (xi) SEQUENCE DESCRIPTION: SEQ ID NO:7:

| Met | Tyr | Val | Trp | Val | Gln | Gln | Pro | Thr | Ala | Leu | Leu | Leu | Leu | Gly | Leu |
| 1 | | | | 5 | | | | | 10 | | | | | 15 | |

| Thr | Leu | Gly | Val | Thr | Ala | Arg | Arg | Leu | Asn | Cys | Val | Lys | His | Thr | Tyr |
| | | | 20 | | | | | 25 | | | | | 30 | | |

| | | | | | | | | | | | | | | |
|---|---|---|---|---|---|---|---|---|---|---|---|---|---|---|
| Pro | Ser | Gly<br>35 | His | Lys | Cys | Cys | Arg<br>40 | Glu | Cys | Gln | Pro<br>45 | Gly | His | Gly | Met |
| Val | Asn<br>50 | Arg | Cys | Asp | His<br>55 | Thr | Arg | Asp | Thr | Leu<br>60 | Cys | His | Pro | Cys | Glu |
| Thr<br>65 | Gly | Phe | Tyr | Asn | Glu<br>70 | Ala | Val | Asn | Tyr | Asp<br>75 | Thr | Cys | Lys | Gln | Cys<br>80 |
| Thr | Gln | Cys | Asn | His<br>85 | Arg | Ser | Gly | Ser | Glu<br>90 | Leu | Lys | Gln | Asn | Cys<br>95 | Thr |
| Pro | Thr | Gln | Asp<br>100 | Thr | Val | Cys | Arg | Cys<br>105 | Arg | Pro | Gly | Thr | Gln<br>110 | Pro | Arg |
| Gln | Asp | Ser<br>115 | Gly | Tyr | Lys | Leu | Gly<br>120 | Val | Asp | Cys | Val | Pro<br>125 | Cys | Pro | Pro |
| Gly | His<br>130 | Phe | Ser | Pro | Gly<br>135 | Asn | Gln | Ala | Cys | Lys<br>140 | Pro | Trp | Thr | Asn |
| Cys<br>145 | Thr | Leu | Ser | Gly | Lys<br>150 | Gln | Thr | Arg | His | Pro<br>155 | Ala | Ser | Asp | Ser | Leu<br>160 |
| Asp | Ala | Val | Cys | Glu<br>165 | Asp | Arg | Ser | Leu | Leu<br>170 | Ala | Thr | Leu | Leu | Trp<br>175 | Glu |
| Thr | Gln | Arg | Pro<br>180 | Thr | Phe | Arg | Pro | Thr<br>185 | Thr | Val | Gln | Ser | Thr<br>190 | Thr | Val |
| Trp | Pro | Arg<br>195 | Thr | Ser | Glu | Leu | Pro<br>200 | Ser | Thr | Pro | Thr | Leu<br>205 | Val | | |

( 2 ) INFORMATION FOR SEQ ID NO:8:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i i ) IMMEDIATE SOURCE:
        ( B ) CLONE: Oligo NOPVU1

( x i ) SEQUENCE DESCRIPTION: SEQ ID NO:8:

CTTCTGACAA CTATAGGCGG ACCGAAGG                      28

( 2 ) INFORMATION FOR SEQ ID NO:9:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i i ) IMMEDIATE SOURCE:
        ( B ) CLONE: Oligo NOFCR1

( x i ) SEQUENCE DESCRIPTION: SEQ ID NO:9:

CCAGCACCT GAAGCCGAGG GCGCGCCGTC AGTCTTCC            37

( 2 ) INFORMATION FOR SEQ ID NO:10:

( i ) SEQUENCE CHARACTERISTICS:
   ( A ) LENGTH: 1317 base pairs
   ( B ) TYPE: nucleic acid
   ( C ) STRANDEDNESS: single
   ( D ) TOPOLOGY: linear ( i i ) MOLECULE TYPE: cDNA ( i i i ) HYPOTHETICAL: NO ( i v ) ANTI-SENSE: NO ( v i i ) IMMEDIATE SOURCE:
   ( B ) CLONE: MOX40Fc Mutein ( i x ) FEATURE:
   ( A ) NAME/KEY: CDS
   ( B ) LOCATION: 1..1317

( x i ) SEQUENCE DESCRIPTION: SEQ ID NO:10:

```
ATG TAT GTG TGG GTT CAG CAG CCC ACA GCC CTT CTG CTG CTG GGA CTC        48
Met Tyr Val Trp Val Gln Gln Pro Thr Ala Leu Leu Leu Leu Gly Leu
 1               5                  10                  15

ACA CTT GGA GTT ACA GCA AGG CGG CTC AAC TGT GTT AAA CAT ACC TAC        96
Thr Leu Gly Val Thr Ala Arg Arg Leu Asn Cys Val Lys His Thr Tyr
            20                  25                  30

CCC AGT GGT CAC AAG TGC TGT CGT GAG TGC CAG CCA GGC CAT GGT ATG       144
Pro Ser Gly His Lys Cys Cys Arg Glu Cys Gln Pro Gly His Gly Met
        35                  40                  45

GTG AAC CGC TGT GAT CAT ACC AGG GAT ACT CTA TGT CAT CCG TGT GAG       192
Val Asn Arg Cys Asp His Thr Arg Asp Thr Leu Cys His Pro Cys Glu
    50                  55                  60

ACT GGC TTC TAC AAT GAA GCT GTC AAT TAT GAT ACC TGC AAG CAG TGT       240
Thr Gly Phe Tyr Asn Glu Ala Val Asn Tyr Asp Thr Cys Lys Gln Cys
65                  70                  75                  80

ACA CAG TGC AAC CAT CGA AGT GGA AGT GAA CTC AAG CAG AAT TGC ACA       288
Thr Gln Cys Asn His Arg Ser Gly Ser Glu Leu Lys Gln Asn Cys Thr
                85                  90                  95

CCT ACT CAG GAT ACT GTC TGC AGA TGT AGA CCA GGC ACC CAA CCT CGG       336
Pro Thr Gln Asp Thr Val Cys Arg Cys Arg Pro Gly Thr Gln Pro Arg
            100                 105                 110

CAG GAC AGC GGC TAC AAG CTT GGA GTT GAC TGT GTT CCC TGC CCT CCT       384
Gln Asp Ser Gly Tyr Lys Leu Gly Val Asp Cys Val Pro Cys Pro Pro
        115                 120                 125

GGC CAC TTT TCT CCA GGC AAC AAC CAG GCC TGC AAG CCC TGG ACC AAT       432
Gly His Phe Ser Pro Gly Asn Asn Gln Ala Cys Lys Pro Trp Thr Asn
    130                 135                 140

TGT ACC TTA TCT GGA AAG CAG ACC CGC CAC CCA GCC AGT GAC AGC TTG       480
Cys Thr Leu Ser Gly Lys Gln Thr Arg His Pro Ala Ser Asp Ser Leu
145                 150                 155                 160

GAC GCA GTC TGT GAG GAC AGA AGC CTC CTG GCC ACA CTG CTC TGG GAG       528
Asp Ala Val Cys Glu Asp Arg Ser Leu Leu Ala Thr Leu Leu Trp Glu
                165                 170                 175

ACC CAG CGC CCT ACA TTC AGG CCA ACC ACT GTC CAA TCC ACC ACA GTC       576
Thr Gln Arg Pro Thr Phe Arg Pro Thr Thr Val Gln Ser Thr Thr Val
            180                 185                 190

TGG CCC AGG ACT TCT GAG TTG CCC TCT ACA CCC ACC TTG GTG GAG CCC       624
Trp Pro Arg Thr Ser Glu Leu Pro Ser Thr Pro Thr Leu Val Glu Pro
        195                 200                 205

AGA TCT TGT GAC AAA ACT CAC ACA TGC CCA CCG TGC CCA GCA CCT GAA       672
Arg Ser Cys Asp Lys Thr His Thr Cys Pro Pro Cys Pro Ala Pro Glu
    210                 215                 220

GCC GAG GGC GCG CCG TCA GTC TTC CTC TTC CCC CCA AAA CCC AAG GAC       720
Ala Glu Gly Ala Pro Ser Val Phe Leu Phe Pro Pro Lys Pro Lys Asp
225                 230                 235                 240
```

```
ACC CTC ATG ATC TCC CGG ACC CCT GAG GTC ACA TGC GTG GTG GTG GAC    768
Thr Leu Met Ile Ser Arg Thr Pro Glu Val Thr Cys Val Val Val Asp
        245             250                 255

GTG AGC CAC GAA GAC CCT GAG GTC AAG TTC AAC TGG TAC GTG GAC GGC    816
Val Ser His Glu Asp Pro Glu Val Lys Phe Asn Trp Tyr Val Asp Gly
            260             265                 270

GTG GAG GTG CAT AAT GCC AAG ACA AAG CCG CGG GAG GAG CAG TAC AAC    864
Val Glu Val His Asn Ala Lys Thr Lys Pro Arg Glu Glu Gln Tyr Asn
        275             280                 285

AGC ACG TAC CGG GTG GTC AGC GTC CTC ACC GTC CTG CAC CAG GAC TGG    912
Ser Thr Tyr Arg Val Val Ser Val Leu Thr Val Leu His Gln Asp Trp
    290                 295             300

CTG AAT GGC AAG GAG TAC AAG TGC AAG GTC TCC AAC AAA GCC CTC CCA    960
Leu Asn Gly Lys Glu Tyr Lys Cys Lys Val Ser Asn Lys Ala Leu Pro
305             310             315                 320

GCC CCC ATC GAG AAA ACC ATC TCC AAA GCC AAA GGG CAG CCC CGA GAA   1008
Ala Pro Ile Glu Lys Thr Ile Ser Lys Ala Lys Gly Gln Pro Arg Glu
                325             330                 335

CCA CAG GTG TAC ACC CTG CCC CCA TCC CGG GAT GAG CTG ACC AAG AAC   1056
Pro Gln Val Tyr Thr Leu Pro Pro Ser Arg Asp Glu Leu Thr Lys Asn
            340                 345             350

CAG GTC AGC CTG ACC TGC CTG GTC AAA GGC TTC TAT CCC AGC GAC ATC   1104
Gln Val Ser Leu Thr Cys Leu Val Lys Gly Phe Tyr Pro Ser Asp Ile
        355                 360             365

GCC GTG GAG TGG GAG AGC AAT GGG CAG CCG GAG AAC AAC TAC AAG ACC   1152
Ala Val Glu Trp Glu Ser Asn Gly Gln Pro Glu Asn Asn Tyr Lys Thr
    370                 375             380

ACG CCT CCC GTG CTG GAC TCC GAC GGC TCC TTC TTC CTC TAC AGC AAG   1200
Thr Pro Pro Val Leu Asp Ser Asp Gly Ser Phe Phe Leu Tyr Ser Lys
385                 390             395                 400

CTC ACC GTG GAC AAG AGC AGG TGG CAG CAG GGG AAC GTC TTC TCA TGC   1248
Leu Thr Val Asp Lys Ser Arg Trp Gln Gln Gly Asn Val Phe Ser Cys
                405             410                 415

TCC GTG ATG CAT GAG GCT CTG CAC AAC CAC TAC ACG CAG AAG AGC CTC   1296
Ser Val Met His Glu Ala Leu His Asn His Tyr Thr Gln Lys Ser Leu
            420             425                 430

TCC CTG TCT CCG GGT AAA TGA                                       1317
Ser Leu Ser Pro Gly Lys
        435
```

( 2 ) INFORMATION FOR SEQ ID NO:11:

( i ) SEQUENCE CHARACTERISTICS:
        ( A ) LENGTH: 438 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

```
Met Tyr Val Trp Val Gln Gln Pro Thr Ala Leu Leu Leu Gly Leu
1               5                   10                  15

Thr Leu Gly Val Thr Ala Arg Arg Leu Asn Cys Val Lys His Thr Tyr
            20              25                  30

Pro Ser Gly His Lys Cys Cys Arg Glu Cys Gln Pro Gly His Gly Met
        35              40                  45

Val Asn Arg Cys Asp His Thr Arg Asp Thr Leu Cys His Pro Cys Glu
    50                  55                  60

Thr Gly Phe Tyr Asn Glu Ala Val Asn Tyr Asp Thr Cys Lys Gln Cys
65                  70                  75                  80
```

```
Thr Gln Cys Asn His Arg Ser Gly Ser Glu Leu Lys Gln Asn Cys Thr
                 85                  90                  95

Pro Thr Gln Asp Thr Val Cys Arg Cys Arg Pro Gly Thr Gln Pro Arg
            100                 105                 110

Gln Asp Ser Gly Tyr Lys Leu Gly Val Asp Cys Val Pro Cys Pro Pro
            115                 120                 125

Gly His Phe Ser Pro Gly Asn Gln Ala Cys Lys Pro Trp Thr Asn
        130                 135                 140

Cys Thr Leu Ser Gly Lys Gln Thr Arg His Pro Ala Ser Asp Ser Leu
145             150                 155                 160

Asp Ala Val Cys Glu Asp Arg Ser Leu Leu Ala Thr Leu Leu Trp Glu
                165                 170                 175

Thr Gln Arg Pro Thr Phe Arg Pro Thr Thr Val Gln Ser Thr Thr Val
            180                 185                 190

Trp Pro Arg Thr Ser Glu Leu Pro Ser Thr Pro Thr Leu Val Glu Pro
            195                 200                 205

Arg Ser Cys Asp Lys Thr His Thr Cys Pro Pro Cys Pro Ala Pro Glu
    210                 215                 220

Ala Glu Gly Ala Pro Ser Val Phe Leu Phe Pro Pro Lys Pro Lys Asp
225             230                 235                 240

Thr Leu Met Ile Ser Arg Thr Pro Glu Val Thr Cys Val Val Val Asp
                245                 250                 255

Val Ser His Glu Asp Pro Glu Val Lys Phe Asn Trp Tyr Val Asp Gly
            260                 265                 270

Val Glu Val His Asn Ala Lys Thr Lys Pro Arg Glu Glu Gln Tyr Asn
        275                 280                 285

Ser Thr Tyr Arg Val Val Ser Val Leu Thr Val Leu His Gln Asp Trp
    290                 295                 300

Leu Asn Gly Lys Glu Tyr Lys Cys Lys Val Ser Asn Lys Ala Leu Pro
305                 310                 315                 320

Ala Pro Ile Glu Lys Thr Ile Ser Lys Ala Lys Gly Gln Pro Arg Glu
                325                 330                 335

Pro Gln Val Tyr Thr Leu Pro Pro Ser Arg Asp Glu Leu Thr Lys Asn
            340                 345                 350

Gln Val Ser Leu Thr Cys Leu Val Lys Gly Phe Tyr Pro Ser Asp Ile
            355                 360                 365

Ala Val Glu Trp Glu Ser Asn Gly Gln Pro Glu Asn Asn Tyr Lys Thr
        370                 375                 380

Thr Pro Pro Val Leu Asp Ser Asp Gly Ser Phe Phe Leu Tyr Ser Lys
385             390                 395                 400

Leu Thr Val Asp Lys Ser Arg Trp Gln Gln Gly Asn Val Phe Ser Cys
                405                 410                 415

Ser Val Met His Glu Ala Leu His Asn His Tyr Thr Gln Lys Ser Leu
            420                 425                 430

Ser Leu Ser Pro Gly Lys
            435
```

( 2 ) INFORMATION FOR SEQ ID NO:12:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA

```
        ( i i i ) HYPOTHETICAL: NO ( i v ) ANTI-SENSE: NO ( v i i ) IMMEDIATE SOURCE:
                  ( B ) CLONE: Primer #1

( x i ) SEQUENCE DESCRIPTION: SEQ ID NO:12:

GATCTTGGAA CGAGACGACC TGCT                                              24

( 2 ) INFORMATION FOR SEQ ID NO:13:

( i ) SEQUENCE CHARACTERISTICS:
                  ( A ) LENGTH: 20 base pairs
                  ( B ) TYPE: nucleic acid
                  ( C ) STRANDEDNESS: single
                  ( D ) TOPOLOGY: linear ( i i ) MOLECULE TYPE: cDNA ( i i i ) HYPOTHETICAL: NO ( i v ) ANTI-SENSE: NO ( v i i ) IMMEDIATE SOURCE:
                  ( B ) CLONE: Primer #2

( x i ) SEQUENCE DESCRIPTION: SEQ ID NO:13:

AGCAGGTCGT CTCGTTCCAA                                                   20
```